(12) United States Patent
Flyvbjerg et al.

(10) Patent No.: US 8,314,059 B2
(45) Date of Patent: Nov. 20, 2012

(54) DIABETIC NEPHROPATHY THERAPIES

(75) Inventors: Allan Flyvbjerg, Odder (DK); Guangjie Guo, Foster City, CA (US); David Y. Liu, Palo Alto, CA (US); Thomas B. Neff, Atherton, CA (US); Noelynn A. Oliver, Los Altos, CA (US); William R. Usinger, Lafayette, CA (US); Qingjian Wang, Foster City, CA (US)

(73) Assignee: FibroGen, Inc., San Francisco, CA (US)

( * ) Notice: Subject to any disclaimer, the term of this patent is extended or adjusted under 35 U.S.C. 154(b) by 0 days.

(21) Appl. No.: 12/802,373

(22) Filed: Jun. 3, 2010

(65) Prior Publication Data

US 2010/0291098 A1 Nov. 18, 2010

Related U.S. Application Data

(63) Continuation of application No. 11/057,323, filed on Feb. 11, 2005, now abandoned.

(60) Provisional application No. 60/620,802, filed on Oct. 20, 2004, provisional application No. 60/578,401, filed on Jun. 9, 2004, provisional application No. 60/561,018, filed on Apr. 8, 2004, provisional application No. 60/544,121, filed on Feb. 11, 2004.

(51) Int. Cl.
*A61K 38/00* (2006.01)
*A61K 38/17* (2006.01)

(52) U.S. Cl. ..................... 514/1.1; 514/21.92

(58) Field of Classification Search ............. 514/2, 21, 514/866, 1.1, 21.92; 435/326
See application file for complete search history.

(56) References Cited

U.S. PATENT DOCUMENTS

| | | | |
|---|---|---|---|
| 5,408,040 | A | 4/1995 | Grotendorst et al. |
| 6,358,741 | B1 | 3/2002 | Schmidt et al. |
| 6,562,618 | B1 | 5/2003 | Tamatani et al. |
| 2003/0153524 | A1 | 8/2003 | Hinton et al. |
| 2005/0059629 | A1 | 3/2005 | Gaarde et al. |

FOREIGN PATENT DOCUMENTS

| | | |
|---|---|---|
| WO | WO-96/38172 A1 | 12/1996 |
| WO | WO-99/33878 A1 | 7/1999 |
| WO | WO-00/13706 A1 | 3/2000 |
| WO | WO-00/35936 A1 | 6/2000 |
| WO | WO-03/053340 A2 | 7/2003 |
| WO | WO-2004/108764 A3 | 12/2004 |
| WO | WO-2005/038013 A1 | 4/2005 |

OTHER PUBLICATIONS

Adler, Sharon G., et al., "Glomerular mRNAs in Human Type 1 Diabetes: Biochemical Evidence for Microalbuminuria as a Manifestation of Diabetic Nephropathy," Kidney Int (2001) 60:2330-2336.

Berg, U.B., et al., "Kidney Morphological Changes in Relation to Long-Term Renal Function and Metabolic Control in Adolescents With IDDM," Diabetologia (1998) 41:1047-1056.
Brosius, Frank C. III, "Trophic Factors and Cytrokines in Early Diabetic Glomerulopathy," Experimental Diab Res (2003) 4:225-233.
De Vriese, An S., "Antibodies Against Vascular Endothelial Growth Factor Improve Early Renal Dysfunction in Experimental Diabetes," J Am Soc Nephrol (2001) 12:993-1000.
Fioretta, P., "Patterns of Renal Injury in NIDDM Patients With Microalbuminaria," Diabetologia (1996) 39:1569-1576.
Flyvjberg, Allan, "Amelioration of Long-Term Renal Changes in Obese Type-2 Diabetic Mice by a Neutralizing Vascular Endothelial Growth Factor Antibody," Diabetes (2002) 51:3090-3094.
Gilbert, Richard E., et al., "Urinary Connective Tissue Growth Factor Excretion in Patients With Type I Diabetes and Nephropathy," Diabetes Care (2003) 26(9):2632-2636.
Ito, Yasuhiko, et al., "Human Urinary CTGF (CCN2) as a Predictor of Progression of Chronic Renal Diseases," J Am Soc Nephrol (2003) 14:153A.
Jerums, George, et al., "Evolving Concepts in Advanced Glycation, Diabetic Nephropathy, and Diabetic Vascular Disease," Archives of Biochem and Biophysics (2003) 419:55-62.
Liu, Bi-Cheng, et al., "Mechanisms of Irbesartan in Prevention of Renal Lesion in Streptozotocin-Induced Diabetic Rats," Acta Pharmacol Sin (2003) 24(1):67-72.
Liu, Bi-Cheng, et al., "Role of Connective Tissue Growth Factor in Mediating Hypertrophy of Human Proximal Tubular Cells Induced by Angiotensin II," Am J Nephrol (2003) 23:429-437.
Makino, Hisashi, et al., "Roles of Connective Tissue Growth Factor and Prostanoids in Early Streptozotocin-Induced Diabetic Rat Kidney: The Effect of Aspirin Treatment," Clin Exp Nephrol (2003) 7:33-40.
Matsuoka, Hiroto, et al., "A p38 MAPK Inhibitor, FR-167653, Ameliorates Murine Bleomycin-Induced Pulmonary Fibrosis," Am J Physiol Lung Cell Mol Physiol (2002) 283:L103-L112.
Riser, Bruce L., et al., "Urinary CCN2 (CTGF) as a Possible Predictor of Diabetic Nephropathy: Preliminary Report," Kidney Int (2003) 64:451-458.
Ruperez, Monica, et al., "Angiotensin II Increases Connective Tissue Growth Factor in the Kidney," Am J Pathology (2003) 163(5):1937-1947.
Shimo, Tsuyoshi, et al., "Inhibition of Endogenous Expression of Connective Tissue Growth Factor by Its Antisense Oligonucleotide and Antisense RNA Suppresses Proliferation and Migration of Vascular Endothelial Cells," Biochem (1998) 124:130-140.
Tikellis, Christos, et al., "Connective Tissue Growth Factor is Up-Regulated in the Diabetic Retina: Amelioration by Angiotensin-Converting Enzyme Inhibition," Endocrinology (2004) 145(2):860-866.
Wahab, Nadia Abdel, et al., "Role of Connective Tissue Growth Factor in the Pathogenesis of Diabetic Nephropathy," Biochem J (2001) 359:77-87.
Ziyadeh, Fuad N., "Long-Term Prevention of Renal Insufficiency, Excess Matrix Gene Expression and Glomerular Mesangial Matrix Expansion by Treatment With Monoclonal Antitransforming Growth Factor-β Antibody in db/db Diabetic Mice," PNAS (2000) 97(14):8015-8020.

*Primary Examiner* — Kevin E Weddington
(74) *Attorney, Agent, or Firm* — Leanne C. Price, Esq.; Paul Borchardt

(57) ABSTRACT

The present invention relates to methods and compounds for treating specific early stage aspects and late stage aspects of diabetic nephropathy. Methods and compounds for treating various physiological features associated with early stage and with late stage diabetic nephropathy are also provided.

4 Claims, 9 Drawing Sheets

DIABETIC NEPHROPATHY THERAPIES

This application is a continuation of U.S. application Ser. No. 11/057,323 filed on 11 Feb. 2005 and claims the benefit of U.S. Provisional Application Ser. No. 60/544,121 filed on 11 Feb. 2004, U.S. Provisional Application Ser. No. 60/561,018 filed on 8 Apr. 2004, U.S. Provisional Application Ser. No. 60/578,401 filed on 9 Jun. 2004, and U.S. Provisional Application Ser. No. 60/620,802 filed on 20 Oct. 2004, each of which is incorporated by reference herein it its entirety.

FIELD OF THE INVENTION

The present invention relates to methods and compounds for treating specific early stage aspects and late stage aspects of diabetic nephropathy. Methods and compounds for treating various physiological features associated with early stage and with late stage diabetic nephropathy are also provided.

BACKGROUND OF THE INVENTION

A renal disorder is any alteration in normal physiology and function of the kidney. Renal disorders can result from a wide range of acute and chronic conditions and events, including physical, chemical, or biological injury, insult, or trauma, disease, such as, for example, hypertension, diabetes, congestive heart failure, lupus, sickle cell anemia, and various inflammatory and autoimmune diseases, HIV-associated nephropathies, etc. Renal disorders can lead to reduced kidney function, hypertension, and renal failure, seriously compromising quality of life, sometimes requiring dialysis and in certain circumstances, kidney transplantation.

Diabetic nephropathy is a major long-term complication of diabetes mellitus, and is the leading indication for dialysis and kidney transplantation in the United States. (Marks and Raskin, 1998, Med Clin North Am, 82:877-907.) The development of diabetic nephropathy is seen in 25 to 50% of Type 1 and Type 2 diabetic individuals. Accordingly, diabetic nephropathy is the most common cause of end-stage renal disease and kidney failure in the Western world.

Contributing risk factors associated with the development of diabetic nephropathy (and other renal disorders) in subjects with Type 1 or Type 2 diabetes include hyperglycemia, hypertension, altered glomerular hemodynamics, and increased or aberrant expression of various growth factors, including transforming growth factor-beta (TGFβ), insulin-like growth factor (IGF)-I, vascular endothelial growth factor-a (VEGF-A), and connective tissue growth factor (CTGF). (See, e.g., Flyvbjerg (2000) Diabetologia 43:1205-23; Brosius (2003) Exp Diab Res 4:225-233; Gilbert et al.

Current treatment strategies directed at slowing the progression of diabetic nephropathy using various approaches, including optimized glycemic control (through modification of diet and/or insulin therapy) and hypertension control, have demonstrated varying degrees of success. For example, both angiotensin-converting enzyme (ACE) inhibitors and angiotensin receptor blockers (ARBs), administered to reduce hypertension, have been shown to delay progression or development of nephropathy and macroalbuminuria. Several clinical trials have established the benefits of ACE inhibitors and ARBs in patients with diabetes. However, although ACE inhibitors have been shown to delay renal decline in patients with Type 1 diabetes, the renoprotective effect of these agents in patients with Type 2 diabetes is less clear. (Raij (2003) Am J Hypertens 16:46 S-49S.)

Further, while glycemic and blood pressure control therapies significantly decrease the morbidity and mortality associated with diabetic nephropathy by delaying progression of associated pathologies, such conventional therapies do not adequately halt the progression of the disease and thus fail to provide a complete therapeutic effect. In addition, administration of ACE inhibitors or ARBs, the current standard of care, are not universally effective and only minimally delay, but do not remove, the need for kidney transplantation.

Other treatment strategies have focused on one or more growth factors as therapeutic targets. Therapies directed at inhibiting VEGF or TGFβ, either alone or in combination with ACE inhibitors or ARBs, have been examined. (See, e.g., De Vriese et al. (2001) J Am Soc Nephrol 12:993-1000; Flyvbjerg et al. (2002) Diabetes 51:3090-3094; Ziyadeh et al, (2000) Proc Natl Acad Sci 97:8015-8020; Chen et al. (2003) Biochem Biophys Res Commun 300:16-22; and Benigni et al. (2003) J Am Soc Nephrol 14:1816-1824.) Such therapeutic approaches, however, have not provided amelioration of all aspects of renal pathology (e.g., altered and impaired renal function and structure) associated with diabetic nephropathy. For example, inhibition of TGFβ as a therapeutic target for diabetic nephropathy was not effective at attenuating albuminuria in db/db mice, despite the beneficial effects such treatment had on glomerular matrix expansion. (See Ziyadeh et al, supra) In addition, while administration of anti-VEGF antibodies to diabetic db/db mice provided benefit to diabetes-associated increased permeability in the kidney, only minimal beneficial effects on mesangial expansion were observed. (See Flyvbjerg et al (2002), supra.) Therefore, although such therapies offer promise, alone or in combination, none has resulted in amelioration of both early (e.g., glomerular hyperfiltration, increased glomerular filtration rate. Microalbuminuria, etc.) and late (e.g., decreased glomerular filtration rate, macroalbuminuria, excessive mesangial matrix expansion, etc.) pathological features associated with chronic renal disease, e.g., diabetic nephropathy. Thus, there is a need in the art for a complete therapy for treatment of diabetic nephropathy that ameliorates both early and late stages symptoms and pathologies associated with the development and progression of the disease.

In addition to the above deficiencies, current therapies for diabetic nephropathy have limited applicability/efficacy due to lack of specificity. In particular, VEGF- or TGFβ-targeted therapies may compromise the beneficial activities of these growth factors, such as angiogenesis, tumor suppression, and proper immune system development. For example, while TGFβ has been associated with development of fibrosis, it is also an important mediator of immune development and tumor suppression, suggesting that inhibition of TGFβ might have unwanted and potentially adverse secondary effects. Therefore, there is a need in the art for a more selective therapeutic approach for diabetic nephropathy.

In summary, there is an existing need in the art for a therapeutic approach for treating renal disease, in particular diabetic nephropathy, which is effective at various stages (e.g., early stage and late stage diabetic nephropathy) in the development and progression of the disease. In particular, there is a need for a complete treatment for diabetic nephropathy, one effective in treating both early stage features and late stage features of diabetic nephropathy such as, for example, hyperfiltration (early stage), increased glomerular permeability (early stage), increased glomerular filtration rate (early stage), microalbuminuria (early stage), macroalbuminuria (late stage), and decreased glomerular filtration rate (late stage). There is a need for a therapeutic approach that more completely addresses various and distinct processes associated with development and progression of diabetic nephropathy and other renal diseases. In particular, there is a need for therapies that target both non-fibrotic (e.g., hyperfiltration) and fibrotic (e.g., mesangial matrix expansion) processes associated with diabetic nephropathy. In addition, there is a need for a therapeutic approach for treating renal disease in general, and diabetic nephropathy in particular, that provides both structural and functional benefits.

The present invention addresses these needs by identifying the role of CTGF in various processes associated with the development and progression of renal disorders such as, e.g., diabetic nephropathy, and by providing methods for inhibiting and preventing these processes. The invention further addresses existing needs by providing methods and agents that can be applied to the treatment and prevention of renal diseases, particularly, renal disease associated with diabetes, and most particularly, diabetic nephropathy.

SUMMARY OF THE INVENTION

Figure 1:
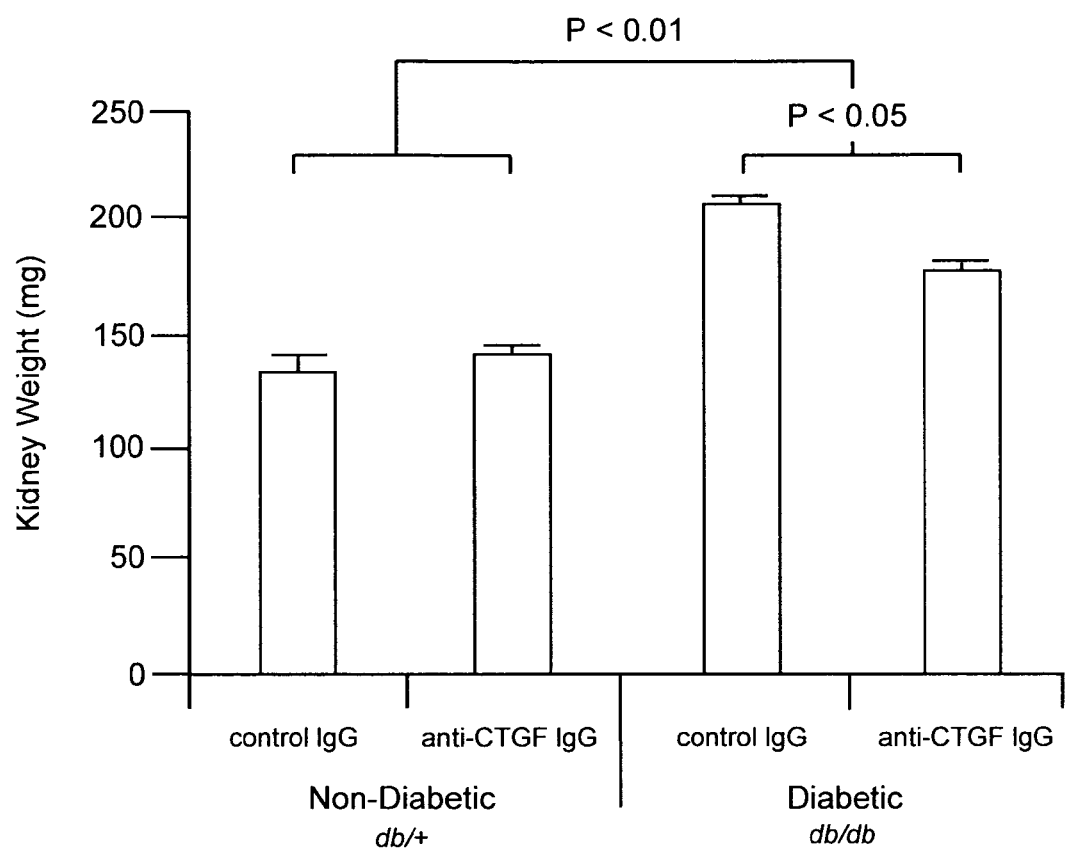
FIG. 1 shows anti-CTGF antibody administration reduced kidney weight increase in diabetic db/db mice.

The present invention relates to methods and compounds for treatment or prevention of specific early stage aspects and late stage aspects of diabetic nephropathy, and for treatment or prevention of various physiological features associated with early stage and with late stage diabetic nephropathy are also provided.

It is specifically contemplated that, in preferred embodiments of each of the methods described below, the preferred subject is a human subject.

In one embodiment, the present invention provides a method for reducing creatinine clearance in a subject having or at risk for having diabetes or early stage diabetic nephropathy, the method comprising administering to the subject a therapeutically effective amount of an agent that inhibits CTGF, thereby reducing creatinine clearance in the subject. Normal creatinine clearance levels in humans are typically about 97 to 137 ml/min. (adult males) and 88 to 128 ml/min (in adult females). Therefore, methods of reducing creatinine clearance levels to these levels or to about these levels are specifically contemplated.

Methods for reducing glomerular hyperfiltration in a subject having or at risk for having diabetes or early stage diabetic nephropathy, the methods comprising administering to the subject a therapeutically effective amount of an agent that inhibits CTGF, are also provided herein, as are methods for reducing glomerular hyperperfusion.

In another aspect, the invention encompasses a method for reducing or preventing kidney weight gain in a subject having or at risk for having diabetes or diabetic nephropathy, the method comprising administering to the subject a therapeutically effective amount of an agent that inhibits CTGF.

The invention further provides methods for normalizing glomerular filtration rate in a subject having or at risk for having diabetes or diabetic nephropathy, the method comprising administering to the subject a therapeutically effective amount of an agent that inhibits CTGF. The diabetic nephropathy can be, for example, early stage, late stage, incipient, or overt diabetic nephropathy. In the case that the diabetic nephropathy is early stage or incipient, the normalization will likely be a decrease in glomerular filtration rate, while in the case that the diabetic nephropathy is late stage or overt, the normalization will likely be an increase. Normal GFR in an adult human subject is about 120 ml/min. In the event that the subject has a GFR elevated above normal levels, and a decrease in GFR would be desired; methods for decreasing the GFR to levels below about 150 mL/min., below about 140 ml./min., below about 130 ml./min, and to about 120 ml/min. are specifically contemplated. In the event that the subject has GFR impaired or decreased below normal, methods for increasing the GFR to above about 15 ml/min., above about 30 ml/min., above about 60 mL/min., above about 90 ml/min., to about 120 ml/min.

In another embodiment, the invention provides a method for reducing glomerular hypertrophy in a subject having or at risk for having diabetes or diabetic nephropathy, including early stage, late stage, incipient, or overt diabetic nephropathy, the method comprising administering to the subject a therapeutically effective amount of an agent that inhibits CTGF.

Methods for reducing proteinuria in a subject having or at risk for having diabetes or diabetic nephropathy are also provided herein, the method comprising administering to the subject a therapeutically effective amount of an agent that inhibits CTGF. The invention additionally encompasses methods for reducing albuminuria in a subject having or at risk for having diabetes or diabetic nephropathy, the method comprising administering to the subject a therapeutically effective amount of an agent that inhibits CTGF. A method for reducing microalbuminuria in a subject having or at risk for having diabetes or diabetic nephropathy, wherein the diabetic nephropathy is early stage or incipient diabetic nephropathy, the method comprising administering to the subject a therapeutically effective amount of an agent that inhibits CTGF, is additionally contemplated, as is a method for reducing macroalbuminuria in a subject having or at risk for having diabetes or diabetic nephropathy, wherein the diabetic nephropathy is late stage or overt, the method comprising administering to the subject a therapeutically effective amount of an agent that inhibits CTGF.

Normal urinary albumin excretion levels in adult humans are typically about 15-30 mg per day. Microalbuminuria is typically diagnosed when a subject has a urinary albumin excretion of about 30-300 mg/day. Macroalbuminuria is typically characterized by urinary albumin excretion of greater than about 300 mg/day. The present invention thus specifically provides methods for decreasing urinary albumin excretion in a subject, the method comprising administering to the subject an effective amount of an agent that inhibits CTGF, having elevated urinary albumin excretion, e.g., urinary albumin excretion elevated above normal levels. Embodiments in which the urinary albumin excretion is reduced to under about 300 mg/day, under about 200 mg/day, under about 100 mg/day, under about 50 mg/day, and, most preferably, under about 30 mg/day are specifically contemplated herein.

In certain aspects, the invention provides a method for reducing BUN levels in a subject having or at risk for having diabetes or diabetic nephropathy, the method comprising administering to the subject a therapeutically effective amount of an agent that inhibits CTGF. Normal BUN levels for adult humans range from 7-20 mg/dL. Therefore, methods for reducing BUN levels to below 20 mg/dL. The invention further provides a method for reducing inulin clearance in a subject having or at risk for having diabetes or diabetic nephropathy, the method comprising administering to the subject a therapeutically effective amount of an agent that inhibits CTGF. In specific aspects, the diabetic nephropathy is late stage diabetic nephropathy or overt diabetic nephropathy.

In yet a further embodiment, the invention provides a method for preventing, reducing the risk of or delaying the onset of diabetic complications in a subject at risk for developing such complications, the method comprising administering to the subject a therapeutically effective amount of an agent that inhibits CTGF. In various embodiments, the diabetic complications include at least one complication selected from the group consisting of increased creatinine clearance, increased or decreased glomerular filtration rate, glomerular basement membrane thickening, glomerular hyperfiltration, glomerular hyperperfusion, glomerular hypertrophy, increased urinary albumin excretion, microalbuminuria, macroalbuminuria, increased BUN levels, increased inulin clearance, kidney weight gain, and impaired kidney function.

The invention also encompasses a method for treating incipient diabetic nephropathy in a subject having or at risk for having incipient diabetic nephropathy, the method comprising administering to the subject a therapeutically effective amount of an agent that inhibits CTGF, and a method for treating early stage diabetic nephropathy in a subject having or at risk for having early stage diabetic nephropathy, the method comprising administering to the subject a therapeutically effective amount of an agent that inhibits CTGF. A method for treating overt diabetic nephropathy in a subject having or at risk for having overt diabetic nephropathy, the method comprising administering to the subject a therapeutically effective amount of an agent that inhibits CTGF, is also contemplated herein.

The present invention contemplates the use of the present methods in combination with other therapies. In one embodiment, the method is used in combination with another therapy, e.g., to further augment therapeutic effect on certain pathological events, etc. The two treatments may be administered at the same time or consecutively, e.g., during a treatment time course or following disease progression and remission. In another embodiment, the method is used in combination with another therapeutic method having a similar or different mode of action, e.g., ACE inhibitors, ARBs, statin, advanced glycation endproduct (AGE) inhibitor, etc. Thus, in a particular embodiment, the present invention provides a method for treating diabetic nephropathy in a subject having or at risk for having diabetic nephropathy, the method comprising administering to the subject a therapeutically effective amount of an agent that inhibits CTGF in combination with an inhibiting amount of an angiotensin converting enzyme inhibitor. The present invention further provides a method for treating diabetic nephropathy in a subject having or at risk for having diabetic nephropathy, the method comprising administering to the subject a therapeutically effective amount of an agent that inhibits CTGF in combination with an inhibiting amount of an angiotensin receptor blocker.

Methods for treating progressive renal failure in a subject the method comprising administering to the subject a therapeutically effective amount of an agent that inhibits CTGF, are provided in one embodiment. In another embodiment, the invention provides a method for reducing the risk or delaying the onset of development of microalbuminuria in a subject, the method comprising administering to the subject a therapeutically effective amount of an agent that inhibits CTGF. In an additional embodiment, a method for reducing the risk or delaying the onset of development of macroalbuminuria in a subject, the method comprising administering to the subject a therapeutically effective amount of an agent that inhibits CTGF, is also provided.

In a particular aspect, the invention relates to the present discovery that CTGF is herein identified as a critical factor in early stage progressive diseases including diabetic kidney complications and vitreoretinal disorders. Therefore, in one aspect, the invention relates to a method for treating or preventing early stage aspects of a progressive disease in a subject having or at risk for having such a disease, the method comprising administering to the subject a therapeutically effective amount of an agent that inhibits CTGF. In a further aspect, the progressive disease is associated with a growth factor other than CTGF, and, in a specific aspect, the other growth factor is VEGF. In one aspect, the progressive disease is a renal disease, and, in a particular aspect, the progressive disease is associated with diabetes or with diabetic complications, or is diabetic nephropathy.

The invention additionally encompasses a method for improving kidney function in a subject having or at risk for having impaired kidney function, the method comprising administering to the subject a therapeutically effective amount of an agent that inhibits CTGF.

As summarized in the preceding description, the invention relates to the discovery that anti-CTGF therapy is effective in treatment or prevention of various physiological features of early stage and late stagy diabetic nephropathy. Accordingly, it is contemplated that the present invention provides methods for treating or preventing a renal disorder associated with at least one of the features selected from the following: increased creatinine clearance; increased glomerular filtration or glomerular hyperfiltration; proteinuria; increased urine albumin excretion; increased glomerular volume; glomerular hypertrophy; increased kidney weight; glomerular basement membrane thickening; reduced glomerular filtration rate; increased BUN levels; and increased inulin clearance. In each case, the methods comprise administering to a subject in need of such treatment an effective amount of an agent that inhibits CTGF. These methods specifically cover administration to a subject of the agent that inhibits CTGF for the express purpose of preventing progression to or development of any one of the above-described complications.

In preferred embodiments of the above-described methods, the subject is a human subject.

In any of the methods described above, it is particularly contemplated that the agent that inhibits CTGF may be a polypeptide, polynucleotide, or small molecule; for example, an antibody that binds to CTGF, an antisense molecule, siRNAs, small molecule chemical compounds, etc. In particular, the present invention contemplates that inhibiting CTGF can be accomplished by any of the means well-known in the art for modulating the expression and activity of CTGF. Use of anti-CTGF agent, for example, a human monoclonal antibody directed against CTGF, is preferred, although any method of inhibiting expression of the gene encoding CTGF, inhibiting production of CTGF, or inhibiting activity of CTGF is contemplated by the present invention. For example, small molecule compounds may be used to inhibit CTGF expression, production, or activity. As CTGF expression is inhibited by cyclic nucleotide, such a compound may include, e.g., a cyclic nucleotide analog or a phosphodiesterase (PDE) inhibitor. (See, e.g., Duncan et al. (1999) FASEB J13:1774-1786.) Further, polynucleotides including small interfering ribonucleic acids (siRNAs), micro-RNAs (miRNAs), ribozymes, and anti-sense sequences may be used in the present methods to inhibit expression and/or production of CTGF. (See, e.g., Kondo et al. (2000) Biochem Biophys Res Commun 278:119-124.) Such techniques are well-known to those of skill in the relevant art. Exemplary antibodies for use in the methods of the present invention are described, e.g., in International Publication No. WO 2004/108764, which is incorporated herein by reference in its entirety.

DESCRIPTION OF THE INVENTION

It is to be understood that the invention is not limited to the particular methodologies, protocols, cell lines, assays, and reagents described herein, as these may vary. It is also to be understood that the terminology used herein is intended to describe particular embodiments of the present invention, and is in no way intended to limit the scope of the present invention as set forth in the appended claims.

It must be noted that as used herein and in the appended claims, the singular forms "a," "an," and "the" include plural references unless context clearly dictates otherwise. Thus, for example, a reference to "a fragment" includes a plurality of such fragments, a reference to an "antibody" is a reference to one or more antibodies and to equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology and pharmacology, within the skill of the art. Such techniques are explained fully in the literature. See, e.g., Gennaro, A. R., ed. (1990) Remington's Pharmaceutical Sciences, 18th ed., Mack Publishing Co.; Colowick, S. et al., eds., Methods In Enzymology, Academic Press, Inc.; Handbook of Experimental Immunology, Vols. I-IV (D. M. Weir and C. C. Blackwell, eds., 1986, Blackwell Scientific Publications); Maniatis, T. et al., eds. (1989) Molecular Cloning: A Laboratory Manual, 2nd edition, Vols. Cold Spring Harbor Laboratory Press; Ausubel, F. M. et al., eds. (1999) Short Protocols in Molecular Biology, 4th edition, John Wiley & Sons; Ream et al., eds. (1998) Molecular Biology Techniques: An Intensive Laboratory Course, Academic Press); PCR (Introduction to Biotechniques Series), 2nd ed. (Newton & Graham eds., 1997, Springer Verlag).

The invention relates in part to the discovery that connective tissue growth factor (CTGF) plays a key role in specific early stage aspects of renal disease including, e.g., glomerular hyperfiltration, increased glomerular permeability, increased glomerular filtration rate, microalbuminuria, etc. CTGF had previously been associated with specific late stage aspects of kidney disease, e.g., glomerulosclerosis and tubulointerstitial fibrosis, but had not been identified as a critical target for affecting various features of early stage renal pathologies. Methods for treating or preventing renal disorders including, e.g., diabetic nephropathy, and methods for treating or preventing associated pathologies are specifically contemplated.

The present invention provides methods and compositions for reducing or ameliorating in a subject complications associated with multiple, distinct pathological processes associated with renal disorders, e.g., diabetic nephropathy, by inhibiting CTGF. In some embodiments, the subject is an animal, more preferably a mammal, and most preferably a human.

The present invention also provides compositions for use in the methods described herein. Such compositions may include small molecule compounds; peptides and proteins including antibodies or functionally active fragments thereof; and polynucleotides including small interfering ribonucleic acids (siRNAs), micro-RNAs (miRNAs), ribozymes, and anti-sense sequences. (See, e.g., Zeng (2003) Proc Natl Acad Sci USA 100:9779-9784; and Kurreck (2003) Eur J Biochem 270:1628-1644.)

The present invention is based in part on the discovery of unexpected benefits of inhibition of CTGF in treatment of multiple and specific aspects of renal disorders, e.g., diabetic nephropathy. The present invention provides data demonstrating that inhibition of CTGF reduced various pathological aspects of renal disease not previously associated with CTGF. In certain aspects, the present invention provides evidence that inhibition of CTGF provides a therapeutic approach to treat or prevent specific physiological aspects of diabetic nephropathy previously associated with biological and pathological activities of VEGF, such as, for example, glomerular hyperfiltration and hyperperfusion.

Diabetic Nephropathy

Diabetes is a major cause of morbidity and mortality worldwide, with approximately 40% of all individuals with diabetes developing diabetic nephropathy, requiring either kidney dialysis or transplantation. Diabetes is the leading cause of end stage renal disease, and therefore, any individual diagnosed with diabetes is at risk for the development of diabetic nephropathy.

Progression of diabetic nephropathy is characterized by a fairly predictable pattern of events. Generally, the time course of development of diabetic nephropathy is as follows. Glomerular hyperfiltration and renal hypertrophy occur in the first years after the onset of diabetes and are reflected by increased glomerular filtration rate (e.g., from a normal glomerular filtration rate of about 120 ml/min to about 150 ml/min in humans). During the first 5 years of diabetes, pathological changes, such as glomerular hypertrophy, thickening of the glomerular basement membrane, and glomerular mesangial volume expansion, are observed. Glomerular filtration rate gradually returns to normal. After 5 to 10 years of diabetes, individuals begin to excrete small amounts of albumin in the urine (microalbuminuria). Microalbuminuria (diabetic individuals with microalbuminuria are referred to as having incipient diabetic nephropathy) is an important predictor of progression to overt diabetic nephropathy (characterized, in part, by macroalbuminuria or overt proteinuria). The basement membrane thickening and glomerular volume expansion seen in early stages of the disease can accumulate in late stage diabetic nephropathy, leading to obliteration of the capillary lumen, and, eventually, to glomerulosclerosis. Once overt diabetic nephropathy is present, a steady decline in the glomerular filtration rate occurs, and approximately half of individuals reach end-stage renal disease in 7 to 10 years.

Clinically, the stages of development and progression of diabetic nephropathy in humans have been well described. Stage I diabetic nephropathy is associated with increased kidney (i.e., glormerular) filtration (i.e., hyperfiltration, resulting from increased blood flow through the kidneys and glomeruli), increased glomerular filtration rate, glomerular hypertrophy, and enlarged kidneys. Stage II diabetic nephropathy is a clinically silent phase associated with continued hyperfiltration and kidney hypertrophy. Thickening of the glomerular basement membrane and mesangial expansion occurs. Stage III diabetic nephropathy (also known as incipient diabetic nephropathy) is associated with microalbuminuria and micro proteinuria. Microalbuminuria is defined as 30 to 300 mg/day urinary albumin in a 24-hour collection, 20-200 µg/min urinary albumin, or 30 to 300 µg/mg creatinine in a spot collection. The kidneys progressively lose the ability to filter waste and blood levels of creatinine and urea-nitrogen increase. Glomerular basement membrane thickening and mesangial expansion continue to occur with increasing severity. Stage IV diabetic nephropathy (also known as overt diabetic nephropathy) is associated with macroalbuminuria (i.e., clinical albuminuria) and creatinine and blood urea-nitrogen (BUN) levels in the blood continue to rise. Macroalbuminuria is defined as greater than 300 mg/day urinary albumin in a 24-hour collection, greater than 200 µg/min urinary albumin, or greater than 300 µg/mg creatinine spot collection. Once overt diabetic nephropathy occurs, glomerular filtration rate gradually falls over a period of several years. Stage V diabetic nephropathy occurs with end-stage renal disease and kidney failure.

Hyperfiltration and Hyperperfusion

Early stage diabetic nephropathy is associated with impaired renal function, characterized in part by glomerular hyperfiltration and hyperperfusion. Glomerular hyperfiltration is a glomerular adaptation to nephron loss associated with hyperglycemia and diabetes. With loss of functioning nephron mass, the remaining functional nephrons hypertrophy and take on an increased workload, thereby attempting to minimize the overall loss of renal function. As a result, glomerular hyperfiltration and hyperperfusion occur.

Glomerular hyperfiltration and hyperperfusion are reflected as increased glomerular filtration rate. Glomerular filtration rate is a measurement of the volume of filtrate made by the kidneys per minute. Measurement of glomerular filtration rate in human subjects has been accepted as the best overall index of kidney function in health and disease. (Smith, Diseases of the kidney and urinary tract, In: Structure and Function in Health and Disease, New York; Oxford Univ. Press, 1951:836-887.) Glomerular filtration rate can be determined by various methods, such as by measuring the urinary clearance of a filtration marker, such as inulin, iothalamate, or iohexol. More commonly, glomerular filtration rate is estimated by determining clearance of creatinine, a protein produced by muscle and released into the blood. Creatinine clearance (often expressed as ml/min) can be determined by comparing the level of creatinine collected in urine over a given period of time, e.g., 12 or 24 hours, with the creatinine level in blood. A typical creatinine clearance rate is about 97 to 137 ml/min in adult males, and about 88 to 128 ml/min in adult females.

In clinical practice, creatinine clearance is most often estimated from the serum creatinine concentration. Creatinine clearance is related directly to the urine creatinine excretion and inversely to serum creatinine concentration. Various formulas that provide estimates of creatinine clearance, and therefore estimates of glomerular filtration rate, using parameters such as serum creatinine concentration, age, sex, and body size, have been developed and are standard in the art. (See, e.g., Cockcroft and Gault (1976) Nephron 16:31-41; Levey et al (1999) Annals of Internal Medicine 130:462-470; Rule et al (2004) Ann Intern Med 141:929-937.)

Methods and compounds of the present invention reduced creatinine clearance in an animal model of diabetes. (See, e.g., Example 1.) Therefore, the present invention provides methods and compounds for reducing creatinine clearance in a subject with increased or elevated creatinine clearance or in which creatinine clearance is elevated above normal levels. The present invention demonstrates that inhibition of CTGF (e.g., by administration of an antibody to CTGF) reduces creatinine clearance associated with nephropathy, and in particular, diabetic nephropathy. Increased creatinine clearance is associated with glomerular hyperfiltration, hyperperfusion, hypertrophy, and increased glomerular filtration rate, and is indicative of altered or impaired renal function in early stages of developing nephropathy, e.g., diabetic nephropathy. In one aspect, the present invention provides methods and compounds for reducing creatinine clearance by inhibiting CTGF. In another aspect, the present invention provides methods and compounds for reducing glomerular creatinine permeability and restoring glomerular selectivity and function by inhibiting CTGF. In another aspect, methods and compounds are provided for treating or preventing glomerular hypertrophy, hyperfiltration, and hyperperfusion associated with hyperglycemia or diabetes by inhibiting CTGF. In yet another aspect, methods and compounds are provided for treating or preventing glomerular hypertrophy, hyperfiltration, and hyperperfusion associated with renal diseases, and, in particular, diabetic nephropathy, by inhibiting CTGF. In one aspect, the renal disease is early stage diabetic nephropathy.

In other aspects, the present invention provides methods and compounds for reducing glomerular filtration rate in a subject with an increased glomerular filtration rate by inhibiting CTGF. In one aspect, the present invention provides methods and compounds for reducing glomerular filtration rate by administering to a subject having or at risk for having an impaired or increased glomerular filtration rate an agent that inhibits CTGF. In one aspect, the impaired glomerular filtration and increased glomerular filtration rate are associated with early stage kidney disease.

In certain embodiments, the present invention provides methods and compounds for treating a renal disorder associated with or characterized by increased creatinine clearance by administering to a subject having or at risk for having the disorder an agent that inhibits CTGF, thus treating or preventing the disorder. In other embodiments, the present invention provides methods and compounds for treating a renal disorder associated with or characterized by increased glomerular filtration or glomerular hyperfiltration by administering to a subject having or at risk for having the disorder an agent that inhibits CTGF, thus treating or preventing the disorder.

Methods and compounds of the present invention were found to increase the glomerular filtration rate in an animal model of late stage diabetic nephropathy. (See Example 3.) Therefore, the present invention provides methods and compounds for increasing or normalizing glomerular filtration rate in a subject with a reduced or impaired glomerular filtration rate or in which the glomerular filtration rate is below normal by inhibiting CTGF. In one aspect, the present invention provides methods and compounds for increasing or normalizing the glomerular filtration rate by administering to a subject having or at risk for having an impaired or reduced glomerular filtration rate an agent that inhibits CTGF. In another aspect, the impaired glomerular filtration rate and reduced glomerular filtration rate are associated with late stage kidney disease or overt diabetic nephropathy.

In one aspect, the present invention provides methods and compounds for treating or preventing a renal disorder associated with impaired glomerular filtration rate and reduced glomerular filtration rate by administering to a subject having or at risk for having the disorder an agent that inhibits CTGF, thus treating or preventing the disorder. In another aspect, the impaired glomerular filtration rate and reduced glomerular filtration rate are associated with, late stage kidney disease.

It is contemplated that the present methods can be applied to improving renal function, normalizing glomerular filtration rate, reducing glomerular hyperfiltration and hyperperfusion, or reducing creatinine clearance in a subject with any clinically accepted standard of measurement indicative of nephropathy or renal disease, or a subject at risk for developing such a renal disorder. In certain embodiments, the subject has diabetic kidney disease. In various embodiments, the subject has stage I kidney disease, stage II kidney disease, stage III kidney disease, stage IV kidney disease, or stage V kidney disease.

The present methods are applied to preventing, reducing, or delaying the onset of renal complications associated with early stage kidney disease in a subject at risk for developing such complications, or to manufacture of a medicament for a subject, preferably a human subject, having any of the disorders and features associated with early stage kidney disease discussed herein. In one aspect, the subject has diabetes. Diabetes can be determined by any measure accepted and utilized by those of skill in the art. A human subject would be diagnosed with diabetes with a blood glucose level above about 200 mg/dL (as determined in a fasting blood glucose test, an oral glucose tolerance test, or a random blood glucose test). Therefore, in certain aspects, it is contemplated that a human subject having a blood glucose level above about 200 mg/dL is a suitable subject for treatment with the methods or use of medicaments provided by the present invention.

Other suitable subjects contemplated for treatment with the present methods have impaired glomerular filtration rate. In one embodiment, the human subject has a glomerular filtration rate above normal glomerular filtration rate, e.g., above about 120 ml/min. Therefore, it is contemplated that a human subject having a glomerular filtration rate above about 120 ml/min, above about 130 ml/min, above about 140 ml/min, or above about 150 ml/min is a suitable subject for treatment with the methods or use of medicaments provided by the present invention. It is further contemplated, in various embodiments, that the methods for reducing glomerular filtration rate in a subject with increased glomerular filtration rate (e.g., in a subject with glomerular hyperfiltration and hyperperfusion) can be applied to reducing glomerular filtration rate in a human subject to a level below about 150 ml/min, below about 140 ml/min, below about 130 mL/min, or to a level of about 120 ml/min.

Methods and compounds of the present invention reduced the increase in kidney weight associated with diabetes and early stage diabetic nephropathy in an animal model of diabetes. (See Example 1.) Therefore, a method for treating or preventing a renal disorder associated with increased kidney weight, the method comprising administering to a subject having or at risk for having the disorder an agent that inhibits CTGF, thus treating or preventing the disorder, is contemplated by the present invention. The invention further contemplates a method for treating or preventing a renal disorder associated with increased glomerular volume, the method comprising administering to a subject having or suspected of having the disorder an agent that inhibits CTGF, thus treating or preventing the disorder.

The present methods and compounds are also applied to preventing, reducing, or delaying the onset of renal complications associated with late stage kidney disease in a subject at risk for developing such complications, or manufacture of a medicament for a subject, preferably a human subject, having any of the disorder and conditions associated with late stage kidney disease discussed herein. In one aspect, the human subject has a glomerular filtration rate below a normal glomerular filtration rate, e.g., below about 120 ml/min. Therefore, it is contemplated that a human subject having a glomerular filtration rate below about 120 ml/min, below about 90 ml/min, below about 60 ml/min, below about 30 ml/min, or below about 15 ml/min is a suitable subject for treatment with the methods or use of medicaments provided by the present invention.

It is further contemplated, in various embodiments, that the methods for increasing glomerular filtration rate in a human subject with reduced or impaired glomerular filtration rate (e.g., in a subject with overt diabetic nephropathy) can be applied to increase glomerular filtration rate to a level above about 15 ml/min, above about 30 ml/min, above about 60 ml/min, above about 90 ml/min, and to a level of about 120 ml/min.

In certain embodiments, the renal disorder is associated with Type 1 or Type 2 diabetes. In other embodiments, the renal disorder is diabetic nephropathy.

Microalbuminuria

Early clinical evidence of nephropathy, including diabetic nephropathy, is the appearance of low but abnormal levels of albumin in the urine, a condition referred to as microalbuminuria.

Individuals with microalbuminuria are referred to as having incipient nephropathy, or, if associated with diabetes, incipient diabetic nephropathy. Diabetic individuals with microalbuminuria have a 42% increased risk of progression to overt diabetic nephropathy compared to those with normoalbuminuria (Bruno et al, 2003, Diabetes Care 26:2150-2155). Therefore, the appearance and development of microalbuminuria in individuals with diabetes is associated with a greatly-increased risk of progression to overt diabetic nephropathy (i.e., macroalbuminuria) and eventual end-stage renal disease and kidney failure. (See, e.g., Mogensen and Christensen (1984) N Engl J Med 311:89-93; Mogensen et al (1983) Diabetes 32[Suppl 2]:64-78; Viberti et al (1982) Lancet 1:1430-1432.)

Microalbuminuria can be determined by various methods, including: (1) measurement of the albumin-to-creatinine ratio in a random spot urine collection; (2) 24-hour urine collection with creatinine, allowing the simultaneous measurement of creatinine clearance; and (3) timed (e.g., 4-hour or overnight) collection. Normal urinary albumin excretion in humans is less than 30 µg/mg creatinine (spot collection), less than 30 mg/24-hours (24-hour collection), or less than 20 µg/min (timed collection). Microalbuminuria in humans is having urinary albumin excretion of 30 to 299 µg/mg creatinine (spot collection), 30 to 299 mg/24-hours (24-hour collection), or 20 to 199 µg/min (timed collection). Macroalbuminuria (e.g., clinical albuminuria) in humans is having urinary albumin excretion of greater than or equal to 300 µg/mg creatinine (spot collection), greater than or equal to 300 mg/24-hours (24-hour collection), or greater than or equal to 200 µg/min (timed collection).

The present invention demonstrates for the first time that inhibition of CTGF (e.g., by administration of an antibody to CTGF) reduces urinary albumin excretion associated with nephropathy, and in particular, diabetic nephropathy. (See, e.g., Example 1.) Increased urinary albumin excretion is associated with changes in glomerular albumin permeability and selectivity, and is indicative of altered or impaired renal function in early stages of developing nephropathy. In one aspect, the present invention provides methods for reducing urinary albumin excretion by inhibiting CTGF. In another aspect, the present invention provides methods for reducing glomerular albumin permeability and restoring glomerular selectivity by inhibiting CTGF. In yet another aspect, the present invention provides methods for reducing microalbuminuria by inhibiting CTGF. By reducing microalbuminuria and urinary albumin excretion, the present methods, therefore, provide a means for treating early stage kidney disease and incipient nephropathy.

As described above, in early stage kidney disease, the onset and development of microalbuminuria (i.e., incipient nephropathy) is associated with an increased risk of development of macroalbuminuia, overt nephropathy, end stage renal disease, and kidney failure in individuals with diabetes. Methods and compositions of the present invention, therefore, are also applied to preventing, reducing, or delaying the onset of or reduce the risk of developing renal complications associated with late stage kidney disease, including macroalbuminuia, overt nephropathy, end stage renal disease, and kidney failure, in a subject at risk for developing such complications The present invention demonstrates that inhibition of CTGF (e.g., by administration of an antibody to CTGF) reduces proteinuria, BUN levels, and creatinine clearance associated with nephropathy. Increased proteinuria, BUN levels, and creatinine clearance are indicative of altered or impaired renal function and development of nephropathy. In one aspect, the present invention provides methods and compounds for reducing proteinuria by inhibiting CTGF. In anther aspect, the present invention provides methods and compounds for reducing BUN levels by inhibiting CTGF. In another aspect, methods and compounds are provided for reducing creatinine clearance by inhibiting CTGF.

The present invention demonstrates that inhibition of CTGF (e.g., by administration of an antibody to CTGF) improves kidney function. As diabetic nephropathy progresses to late stage kidney disease, glomerular filtration rate decline, as measured, for example, by decreased inulin clearance, is indicative of altered or impaired kidney function. The present invention further demonstrates that inhibition of CTGF (e.g., by administration of an antibody to CTGF) improved the impaired or reduced glomerular filtration rate associated with late stage kidney disease. (See Example 3.) In one aspect, the present invention provides methods and compounds for increasing glomerular filtration rate by inhibiting CTGF. In another aspect, the present invention provides methods and compounds for decreasing inulin clearance by inhibiting CTGF. In yet another aspect, methods and compounds are provided for treating or preventing impaired kidney function, in particular impaired kidney function associated with nephropathy, such as diabetic nephropathy, by inhibiting CTGF. In other aspects, the nephropathy is associated with decreased glomerular filtration rate, macroalbuminuria, or overt nephropathy.

Late stage diabetic nephropathy is associated with various pathological and morphological changes in the kidney. Such changes include mesangial expansion, associated with increased matrix production and accumulation of mesangial extracellular matrix; mesangial cell expansion; glomerular basement membrane thickening, which in late stage diabetic nephropathy is associated with glomerulosclerosis; and development of tubulointerstitial fibrosis. (Gilbert et at (1999) Kidney Int 56:1627-1673.) Glomerulosclerosis and tubulointerstitial fibrosis are the structural late stage kidney disease hallmarks of advanced diabetic nephropathy with renal insufficiency, resulting in reduction in glomerular filtration rate and, possibly, end stage renal disease and kidney failure.

Prior to the present invention, CTGF had been associated with features of late stages of renal pathology, specifically, production of excess extracellular matrix, excess mesangial matrix expansion, and development of glomeruloscleorsis and tubulointerstitial fibrosis. (See, e.g., International Publication No. WO 00/13706.) It was thought that other factors, e.g., VEGF, were responsible for processes, pathologies and various features associated with early stage renal disease, e.g., hyperfiltration and increased glomerular permeability. In contrast, the present invention provides data demonstrating that it is CTGF that plays a key role in the development and progression of early stage as well as late stage aspects of nephropathy, and thus represents an ideal target for a complete and effective therapeutic approach to diabetic nephropathy.

The present invention provides methods for treating and preventing various clinical and pathological aspects of early stage as well as late stage diabetic nephropathy. Specifically, methods and compositions of the present invention are useful for treating or preventing glomerular hyperfiltration and mesangial matrix expansion. Therefore, the present invention contemplates methods for treating various aspects of renal disease, including features of early stage diabetic kidney disease, such as, e.g., renal and glomerular hypertrophy and hyperfiltration (measured as increased creatinine clearance, increased urinary albumin excretion, increased glomerular filtration rate, etc.), and features of late stage diabetic kidney disease (decreased glomerular filtration rate, mesangial matrix expansion, basement membrane thickening, etc.).

The present invention provides methods, and compositions for use therein, for treating a disorder or condition wherein connective tissue growth factor (CTGF) is a mediating factor. Several CTGF-associated disorders have been described in the literature; however, until the present invention, CTGF was primarily associated with fibroproliferative conditions, particularly those associated with TGFβ. Although numerous disorders involve fibroproliferative processes, and the treatment of these disorders using therapeutics directed at providing or preventing CTGF activity have been suggested, the present invention extends the understanding and, thus, the use of CTGF-directed therapies to treatment of various non-fibroproliferative conditions and complications associated with diabetic nephropathy and renal disorders.

The methods of the present invention, e.g., inhibiting CTGF, effectively reduce hyperfiltration by the kidney and normalize or restore kidney function as measured, e.g., by glomerular filtration rate, urinary albumin excretion, albuminuria, and/or proteinuria. Thus, the methods and compositions of the present invention can be used to treat patients at risk for diabetic nephropathy, including, for example, early stage diabetic nephropathy and incipient diabetic nephropathy. Such subjects include individuals diagnosed with hyperglycemia, hypertension, and/or diabetes. Additionally, the methods of the present invention can be used to treat patients diagnosed with a kidney disorder such as glomeruloscerosis, glomerularnephritis, or diabetic nephropathy.

The methods of the present invention, e.g., inhibiting CTGF, reduce mesangial matrix expansion and glomerular basement membrane thickening. Thus, the methods of the present invention can be used to treat patients at risk for diabetic nephropathy to prevent albuminuria, reduced glomerular filtration rate, and the like. Such subjects include individuals diagnosed with hyperglycemia, hypertension, and/or diabetes. Additionally, the methods of the present invention can be used to treat patients having overt diabetic nephropathy or another renal disorder such as glomerulosclerosis, glomerularnephritis, etc.

Therefore, in one aspect, the present invention contemplates methods of treating or preventing processes associated with early stage renal disease or late stage renal disease by inhibiting CTGF. These pathological conditions include, for example, hyperfiltration, albuminuria, proteinuria, glomerular hypertrophy, and mesangial volume expansion. Use of the present methods to treat or prevent aspects of early stage and of late stage renal disease previously associated with VEGF and TGFβ is specifically contemplated. As stated above, the methods can be used to treat patients at risk for diabetic nephropathy or an associated pathology, and to treat patients having a renal disorder such as glomerulosclerosis, glomerulonephritis, diabetic nephropathy, etc.

The present invention contemplates the use of the present methods in combination with other therapies. In one embodiment, the method is used in combination with another therapy, e.g., to further augment therapeutic effect on certain pathological events, etc. The two treatments may be administered at the same time or consecutively, e.g., during a treatment time course or following disease progression and remission. In another embodiment, the method is used in combination with another therapeutic method having a similar or different mode of action, e.g., an ACE inhibitor, ARBs, statin, advanced glycation endproduct (AGE) inhibitor, etc. Current therapeutic approaches to treat diabetic nephropathy are known by one of skill in the art, and include, for example, ACE inhibitors, angiotensin receptor blockers, statins, advanced glycation endproduct inhibitors, hepatocyte growth factor gene therapy, pyridoxamine, Enapril, PPAR antagonists, sulfonylureas, matrix metalloproteinase inhibitors, COX-2 inhibitors, pirfenidone, sulodexide, high-dose thiamine and Benfotiamine, calcium channel blockers, etc. Use of any of these therapeutic agents in combination with the use of methods of the present invention is specifically contemplated.

The present invention represents the first time therapeutic efficacy of two distinct pathological aspects associated with renal disease (for example, early stage features and late stage features of diabetic nephropathy) has been demonstrated. Although anti-CTGF therapy is exemplified herein using a human monoclonal antibody directed against CTGF, any method of inhibiting expression of the gene encoding CTGF, inhibiting production of CTGF, or inhibiting activity of CTGF is contemplated by the present invention. For example, small molecule compounds may be used to inhibit CTGF expression, production, or activity. As CTGF expression is inhibited by cyclic nucleotide, such a compound may include, e.g., a cyclic nucleotide analog or a phosphodiesterase (PDE) inhibitor. (See, e.g., Duncan et al. (1999) FASEB J13:1774-1786.) Further, polynucleotides including small interfering ribonucleic acids (siRNAs), micro-RNAs (miRNAs), ribozymes, and anti-sense sequences may be used in the present methods to inhibit expression and/or production of CTGF. (See, e.g., Kondo et al. (2000) Biochem Biophys Res Commun 278:119-124; and Shimo et al., supra.) Such techniques are well-known to those of skill in the relevant art.

The present invention provides exemplary evidence that the methods described herein, using an anti-CTGF monoclonal antibody in animal models of diabetes, provide improvement in creatinine clearance and glomerular hypertrophy, and a decrease in kidney weight, an indicator of TGFβ-induced and CTGF-mediated glomerular fibrosis and mesangial expansion. Thus, the methods of the present invention ameliorate two pathologies contributing to diabetic nephropathy, i.e., mesangial expansion and glomerular filtration.

In certain aspects, the present invention provides methods and compositions for treating a disorder associated with TGFβ by inhibiting CTGF. In other aspects, the present invention provides methods and compositions for treating a disorder associated with VEGF by inhibiting CTGF. In yet other aspects, the present invention provides methods and compositions for treating a disorder associated with TGFβ and VEGF by inhibiting CTGF. It is further contemplated in the present invention methods and compositions for treating a disorder associated with other growth factors, e.g., IGF-1, endothelin, etc.

In one aspect, the present invention provides a method for treating or preventing a renal disorder associated with increased creatinine clearance, the method comprising administering to a subject having or at risk for having the disorder an agent that inhibits CTGF (e.g., inhibits or reduces CTGF expression or CTGF activity), thus treating or preventing the renal disorder. In another aspect, the present invention provides methods for treating or preventing a renal disorder associated with increased glomerular filtration and hyperfiltration by administering to a subject having or at risk for having the disorder an agent that inhibits CTGF, thus treating or preventing the disorder. In another aspect, the present invention provides methods for treating or preventing a renal disorder associated with basement membrane thickening by administering to a subject having or at risk for having the disorder an agent that inhibits CTGF, thus treating or preventing the disorder. In another aspect, the present invention provides methods for treating or preventing a renal disorder associated with increased urine volume by administering to a subject having or at risk for having the disorder an agent that inhibits CTGF, thus treating or preventing the disorder. A method for treating a renal disorder associated with increased urinary albumin excretion by administering to a subject having the disorder or at risk for having the disorder an agent that inhibits CTGF, thus treating or preventing the renal disorder, is also provided.

In one aspect, the present invention provides methods for reducing creatinine clearance in a subject in need of such treatment, the method comprising administering to the subject an agent that inhibits CTGF. Methods for reducing urinary albumin excretion, reducing glomerular filtration and hyperfiltration, reducing glomerular volume expansion, or reducing kidney weight increase in a subject in need of such treatment are also provided, the methods comprising administering to the subject an agent that inhibits CTGF. In one embodiment, the present invention provides a method for treating or preventing proteinuria associated with renal disease, the method comprising administering to a subject having or at risk for having the renal disease an agent that inhibits CTGF. In a further embodiment, the proteinuria is albuminuria. In respective embodiments, the albuminuria is microalbuminuria or macroalbuminuria. In another embodiment, the present invention provides a method for treating or preventing basement membrane thickening in the kidney, the method comprising administering to a subject having or as risk for having basement membrane thickening in the kidney an agent that inhibits CTGF. In yet another embodiment, the present invention provides a method for reducing or preventing increased urine volume by administering to a subject having or at risk for having increased urine volume an agent that inhibits CTGF.

Methods of the present invention include administering to a subject in need a therapeutically effective amount of an agent that inhibits CTGF (e.g., reduces CTGF expression or activity). In certain embodiments, the agent is an antibody to CTGF. In a preferred embodiment, the antibody is a monoclonal antibody to CTGF. In another preferred embodiment, the antibody is a human or humanized antibody to CTGF. In another embodiment, the agent is a small molecule. In another embodiment, the agent is an antisense oligonucleotide.

Various agents that inhibit CTGF have been identified. Antibodies that bind to CTGF are described in U.S. Pat. No. 5,408,040; International Publication No. WO 99/07407; International Publication No. WO 99/33878; and International Publication No. WO 00/35936. An exemplary antibody fur use in the methods of the present invention has been described in International Publication No. WO 2004/108764, incorporated by reference herein in its entirety. Such antibodies, or fragments thereof, can be administered by various means known to those skilled in the art. For example, antibodies are often injected intravenously, intraperitoneally, or subcutaneously.

Small molecule inhibitors of CTGF expression and/or activity have also been described; for example, International Publication No. WO 96/38172 identifies modulators of cAMP such as cholera toxin and 8Br-cAMP as inhibitors of CTGF expression. Therefore, compounds identified as, e.g., prostaglandin and/or prostacyclin analogs such as Iloprost (see, e.g., International Publication No. WO 00/02450; Ricupero et al. (1999) Am J Physiol 277:L1165-1171; also, see Ertl et al.(1992) Am Rev Respir Dis 145:A19), and potentially phosphodiesterase IV inhibitors (see, e.g., Kohyama et al. (2002) Am J Respir Cell Mol Biol 26:694-701), may be used to modulate CTGF expression. Also, inhibitors of serine/threonine mitogen activated protein kinases, particularly p 38, cyclin-dependent kinase, e.g. CDK2, and glycogen synthase kinase (GSK)-3 have also been implicated in decreased CTGF expression. (See, e.g., Matsuoka et al. (2002) Am J Physiol Lung Cell Mol Physiol 283:L103-L112; Yosimichi et al. (2001) Eur J Biochem 268:6058-6065; International Publication No. WO 01/38532; and International Publication No. WO 03/092584.) Such agents can be used to reduce expression of CTGF and thereby ameliorate or prevent the pathological processes induced by CTGF in joint disorders. Such compounds can be formulated and administered according to established procedures within the art.

Antisense technologies, including small interfering ribonucleic acids (siRNAs), micro-RNAs (miRNAs), ribozymes, and anti-sense sequences directed to CTGF expression may also be used to treat joint disorders. (See, e.g., Zeng (2003) Proc Natl Acad Sci USA 100:9779-9784; and Kurreck (2003) Eur J Biochem 270:1628-1644.) Antisense constructs that target CTGF expression have been described and utilized to reduce CTGF expression in various cell types. (See, e.g., International Publication No. WO 96/38172; International Publication No. WO 00/27868; International Publication No. WO 00/35936; International Publication No. WO 03/053340; Kothapalli et al. (1997) Cell Growth Differ 8(1):61-68; Shimo et al. (1998) J Biochem (Tokyo) 124(1):130-140; and Uchio et al. (2004) Wound Repair Regen 12:60-66.) Such antisense constructs can be used to reduce expression of CTGF and thereby ameliorate or prevent the pathological processes induced by CTGF in joint disorders. Such constructs can be designed using appropriate vectors and expressional regulators for cell- or tissue-specific expression and constitutive or inducible expression. Such genetic constructs can be formulated and administered according to established procedures within the art.

Pharmaceutical Formulations and Routes of Administration

The compositions of the present invention can be delivered directly or in pharmaceutical compositions containing excipients, as is well known in the art. Present methods of treatment can comprise administration of an effective amount of a compound of the present invention to a subject having or at risk for diabetic nephropathy; particularly a disorder associated with, for example, glomerular hyperfiltration and hyperperfusion, microalbuminuria, incipient diabetic nephropathy, macroalbuminuria, overt nephropathy, etc. In a preferred embodiment, the subject is a mammalian subject, and in a most preferred embodiment, the subject is a human subject.

An effective amount, e.g., dose, of compound or drug can readily be determined by routine experimentation, as can an effective and convenient route of administration and an appropriate formulation. Various formulations and drug delivery systems are available in the art. (See, e.g., Gennaro, ed. (2000) Remington's Pharmaceutical Sciences, supra; and Hardman, Limbird, and Gilman, eds. (2001) The Pharmacological Basis of Therapeutics, supra.)

Suitable routes of administration may, for example, include oral, rectal, topical, nasal, pulmonary, ocular, intestinal, and parenteral administration. Primary routes for parenteral administration include intravenous, intramuscular, and subcutaneous administration. Secondary routes of administration include intraperitoneal, intra-arterial, intra-articular, intracardiac, intracisternal, intradermal, intralesional, intraocular, intrapleural, intrathecal, intrauterine, and intraventricular administration. The indication to be treated, along with the physical, chemical, and biological properties of the drug, dictate the type of formulation and the route of administration to be used, as well as whether local or systemic delivery would be preferred.

Pharmaceutical dosage forms of a compound of the invention may be provided in an instant release, controlled release, sustained release, or target drug-delivery system. Commonly used dosage forms include, for example, solutions and suspensions, (micro-) emulsions, ointments, gels and patches, liposomes, tablets, dragees, soft or hard shell capsules, suppositories, ovules, implants, amorphous or crystalline powders, aerosols, and lyophilized formulations. Depending on route of administration used, special devices may be required for application or administration of the drug, such as, for example, syringes and needles, inhalers, pumps, injection pens, applicators, or special flasks. Pharmaceutical dosage forms are often composed of the drug, an excipient(s), and a container/closure system. One or multiple excipients, also referred to as inactive ingredients, can be added to a compound of the invention to improve or facilitate manufacturing, stability, administration, and safety of the drug, and can provide a means to achieve a desired drug release profile. Therefore, the type of excipient(s) to be added to the drug can depend on various factors, such as, for example, the physical and chemical properties of the drug, the route of administration, and the manufacturing procedure. Pharmaceutically acceptable excipients are available in the art, and include those listed in various pharmacopoeias. (See, e.g., USP, JP, EP, and BP, FDA web page (www.fda.gov), Inactive Ingredient Guide 1996, and Handbook of Pharmaceutical Additives, ed. Ash; Synapse Information Resources, Inc. 2002.)

Pharmaceutical dosage forms of a compound of the present invention may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions of the present invention can include one or more physiologically acceptable inactive ingredients that facilitate processing of active molecules into preparations for pharmaceutical use.

Proper formulation is dependent upon the desired route of administration. For intravenous injection, for example, the composition may be formulated in aqueous solution, if necessary using physiologically compatible buffers, including, for example, phosphate, histidine, or citrate for adjustment of the formulation pH, and a tonicity agent, such as, for example, sodium chloride or dextrose. For transmucosal or nasal administration, semisolid, liquid formulations, or patches may be preferred, possibly containing penetration enhancers. Such penetrants are generally known in the art. For oral administration, the compounds can be formulated in liquid or solid dosage forms and as instant or controlled/sustained release formulations. Suitable dosage forms for oral ingestion by a subject include tablets, pills, dragees, hard and soft shell capsules, liquids, gels, syrups, slurries, suspensions, and emulsions. The compounds may also be formulated in rectal compositions, such as suppositories or retention enemas, e.g., containing conventional suppository bases such as cocoa butter or other glycerides.

Solid oral dosage forms can be obtained using excipients, which may include, fillers, disintegrants, binders (dry and wet), dissolution retardants, lubricants, glidants, antiadherants, cationic exchange resins, wetting agents, antioxidants, preservatives, coloring, and flavoring agents. These excipients can be of synthetic or natural source. Examples of such excipients include cellulose derivatives, citric acid, dicalcium phosphate, gelatine, magnesium carbonate, magnesium/sodium lauryl sulfate, mannitol, polyethylene glycol, polyvinyl pyrrolidone, silicates, silicium dioxide, sodium benzoate, sorbitol, starches, stearic acid or a salt thereof, sugars (i.e. dextrose, sucrose, lactose, etc.), talc, tragacanth mucilage, vegetable oils (hydrogenated), and waxes. Ethanol and water may serve as granulation aides. In certain instances, coating of tablets with, for example, a taste-masking film, a stomach acid resistant film, or a release-retarding film is desirable. Natural and synthetic polymers, in combination with colorants, sugars, and organic solvents or water, are often used to coat tablets, resulting in dragees. When a capsule is preferred over a tablet, the drug powder, suspension, or solution thereof can be delivered in a compatible hard or soft shell capsule.

In one embodiment, the compounds of the present invention can be administered topically, such as through a skin patch, a semi-solid or a liquid formulation, for example a gel, a (micro-) emulsion, an ointment, a solution, a (nano/micro)-suspension, or a foam. The penetration of the drug into the skin and underlying tissues can be regulated, for example, using penetration enhancers; the appropriate choice and combination of lipophilic, hydrophilic, and amphiphilic excipients, including water, organic solvents, waxes, oils, synthetic and natural polymers, surfactants, emulsifiers; by pH adjustment; and use of complexing agents. Other techniques, such as iontophoresis, may be used to regulate skin penetration of a compound of the invention. Transdermal or topical administration would be preferred, for example, in situations in which local delivery with minimal systemic exposure is desired.

For administration by inhalation, or administration to the nose, the compounds for use according to the present invention are conveniently delivered in the form of a solution, suspension, emulsion, or semisolid aerosol from pressurized packs, or a nebuliser, usually with the use of a propellant, e.g., halogenated carbons derived from methan and ethan, carbon dioxide, or any other suitable gas. For topical aerosols, hydrocarbons like butane, isobutene, and pentane are useful. In the case of a pressurized aerosol, the appropriate dosage unit may be determined by providing a valve to deliver a metered amount. Capsules and cartridges of, for example, gelatin, for use in an inhaler or insufflator, may be formulated. These typically contain a powder mix of the compound and a suitable powder base such as lactose or starch.

Compositions formulated for parenteral administration by injection are usually sterile and, can be presented in unit dosage forms, e.g., in ampoules, syringes, injection pens, or in multi-dose containers, the latter usually containing a preservative. The compositions may take such forms as suspensions, solutions, or emulsions in oily or aqueous vehicles, and may contain formulatory agents, such as buffers, tonicity agents, viscosity enhancing agents, surfactants, suspending and dispersing agents, antioxidants, biocompatible polymers, chelating agents, and preservatives. Depending on the injection site, the vehicle may contain water, a synthetic or vegetable oil, and/or organic co-solvents. In certain instances, such as with a lyophilized product or a concentrate, the parenteral formulation would be reconstituted or diluted prior to administration. Depot formulations, providing controlled or sustained release of a compound of the invention, may include injectable suspensions of nano/micro particles or nano/micro or non-micronized crystals. Polymers such as poly(lactic acid), poly(glycolic acid), or copolymers thereof, can serve as controlled/sustained release matrices, in addition to others well known in the art. Other depot delivery systems may be presented in form of implants and pumps requiring incision.

Suitable carriers for intravenous injection for the molecules of the invention are well-known in the art and include water-based solutions containing a base, such as, for example, sodium hydroxide, to form an ionized compound, sucrose or sodium chloride as a tonicity agent, for example, the buffer contains phosphate or histidine. Co-solvents, such as, for example, polyethylene glycols, may be added. These water-based systems are effective at dissolving compounds of the invention and produce low toxicity upon systemic administration. The proportions of the components of a solution system may be varied considerably, without destroying solubility and toxicity characteristics. Furthermore, the identity of the components may be varied. For example, low-toxicity surfactants, such as polysorbates or poloxamers, may be used, as can polyethylene glycol or other co-solvents, biocompatible polymers such as polyvinyl pyrrolidone may be added, and other sugars and polyols may substitute for dextrose.

For composition useful for the present methods of treatment, a therapeutically effective dose can be estimated initially using a variety of techniques well-known in the art. Initial doses used in animal studies may be based on effective concentrations established in cell culture assays. Dosage ranges appropriate for human subjects can be determined, for example, using data obtained from animal studies and cell culture assays.

A therapeutically effective dose or amount of a compound, agent, or drug of the present invention refers to an amount or dose of the compound, agent, or drug that results in amelioration of symptoms or a prolongation of survival in a subject. Toxicity and therapeutic efficacy of such molecules can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio LD50/ED50. Agents that exhibit high therapeutic indices are preferred.

The effective amount or therapeutically effective amount is the amount of the compound or pharmaceutical composition that will elicit the biological or medical response of a tissue, system, animal, or human that is being sought by the researcher, veterinarian, medical doctor, or other clinician, e.g., reducing creatinine clearance, glomerular hyperfiltration and hyperperfusion, urine albumin excretion, or microalbuminuria, or treatment of early or late stage diabetic nephropathy, etc.

Dosages preferably fall within a range of circulating concentrations that includes the ED50 with little or no toxicity. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects, e.g., regulation of glucose metabolism, decrease in blood glucose levels, etc., i.e., minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

The amount of agent or composition administered may be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack, or glass and rubber stoppers such as in vials. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

These and other embodiments of the present invention will readily occur to those of ordinary skill in the art in view of the disclosure herein.

EXAMPLES

The invention will be further understood by reference to the following examples, which are intended to be purely exemplary of the invention. These examples are provided solely to illustrate the claimed invention. The present invention is not limited in scope by the exemplified embodiments, which are intended as illustrations of single aspects of the invention only. Any methods which are functionally equivalent are within the scope of the invention. Various modifications of the invention in addition to those described herein will become apparent to those skilled in the art from the foregoing description and accompanying figures. Such modifications are intended to fall within the scope of the appended claims.

Example 1

Treatment of Early Stage Features of Diabetic Nephropathy

The methods of the invention were used to demonstrate broad-spectrum efficacy in an animal model for certain aspects of early stage diabetic nephropathy as follows. Eight-week-old mice having a loss-of-function mutation in the leptin receptor (Ob-R; encoded by the db gene) were obtained from Harlan, Indianapolis Ind. These db/db mice serve as an animal model of obese type 2 diabetes, and, in particular, a model of obese type 2 diabetic nephropathy characterized by early aspects of diabetic nephropathy, including, for example, kidney hyperfiltration and proteinuria with minimal development of interstitial fibrosis. This is an animal model of early stage diabetic nephropathy rather than late stage diabetic nephropathy, as evidenced by the minimal development of interstitial fibrosis. Homozygous db/db (diabetic) are hyperglycemic at 8 weeks of age. Homozygous db/db (diabetic) and heterozygous db/+(non-diabetic) animals were treated (intraperitoneal injection) with either anti-CTGF monoclonal antibody ($\alpha$CTGF) (prepared as described in International Publication No. WO 2004/108764 or by the cell line identified by ATCC Accession No. PTA-6006, deposited 20 May 2004) or control human IgG (cIgG). In all animals, an initial injection of 300 $\mu$g of antibody was followed by 100 $\mu$g doses administered 3 times per week for 60 days. Blood samples were collected and body weights were measured at the beginning of and periodically throughout the treatment period. Food consumption was also recorded.

Table 1 below shows the mean body weight (BW), blood glucose level (BG), and food consumption (FC) at day 0 and day 60 in cIgG-treated db/+mice, $\alpha$CTGF-treated db/+mice, cIgG-treated diabetic db/db mice, and $\alpha$CTGF-treated db/db mice. All data are expressed as Mean±SEM. The number of mice per group (n) ranged from 9 to 15. Non-diabetic (db/+) animals that presented with polycystic kidneys were excluded from the analysis. As shown in Table 1, a clear distinction existed between the diabetic (db/db) animals and the non-diabetic (db/+) animals with respect to body weight, blood glucose levels, and food consumption. Treatment with either anti-CTGF antibody or cIgG did not significantly affect overall weight gain, blood glucose levels, or food consumption in either diabetic (db/db) or non-diabetic (db/+) animals.

TABLE 1

| Group, Treatment (no. of animals) | Day 0 | | | Day 60 | | |
| --- | --- | --- | --- | --- | --- | --- |
| | BW (g) | BG (mM) | FC (g/24 h) | BW (g) | BG (mM) | FC (g/24 h) |
| db/+, cIgG (n = 11) | 20.6 ± 0.3 | 6.3 ± 0.2 | 4.8 ± 0.1 | 22.4 ± 0.4 | 6.0 ± 0.2 | 5.0 ± 0.1 |
| db/+, $\alpha$CTGF (n = 9) | 20.2 ± 0.4 | 6.1 ± 0.2 | 4.7 ± 0.2 | 21.6 ± 0.3 | 6.2 ± 0.1 | 5.1 ± 0.2 |

TABLE 1-continued

| | Day 0 | | | Day 60 | | |
|---|---|---|---|---|---|---|
| Group, Treatment (no. of animals) | BW (g) | BG (mM) | FC (g/24 h) | BW (g) | BG (mM) | FC (g/24 h) |
| db/db, cIgG (n = 15) | 39.4 ± 0.6* | 16.7 ± 1.0* | 10.0 ± 0.2* | 47.1 ± 1.0* | 22.1 ± 0.8* | 10.8 ± 0.2* |
| db/db, αCTGF (n = 14) | 38.0 ± 1.0* | 15.8 ± 0.7* | 10.2 ± 0.1* | 47.7 ± 1.2* | 21.7 ± 0.8* | 10.5 ± 0.1* |

Data are expressed as mean ± SEM.
*$P < 0.01$ vs. db/+ mice.

Inhibition of Progression of Early Stage Features of Diabetic Nephropathy

Following the anti-CTGF antibody treatment period described above, various measurements of kidney function and nephropathy were obtained, including kidney weight, creatinine clearance, urinary albumin excretion, and urine volume. Table 2 below shows the mean kidney weight (KW), creatinine clearance (CrC1), and 24-hour urinary albumin excretion (UAE) at day 60 in cIgG-treated db/+mice, αCTGF-treated db/+mice, cIgG-treated db/db mice, and αCTGF-treated db/db mice. All data are expressed as Mean±SEM. The number of mice per group (n) ranged from 9 to 15. As stated above, non-diabetic (db/+) animals that presented with polycystic kidneys were excluded from the analysis.

TABLE 2

| Group, Treatment (no. of animals) | KW (mg) | CrCl (ml/h) | UAE (μg/24 h) |
|---|---|---|---|
| db/+, cIgG (n = 11) | 133.8 ± 5.1 | 2.17 ± 0.29 | 0.30 ± 0.02 |
| db/+, αCTGF (n = 9) | 141.0 ± 4.3 | 2.37 ± 0.19 | 0.23 ± 0.04 |
| db/db, cIgG (n = 15) | 207.8 ± 3.9** | 5.39 ± 0.36** | 2.52 ± 0.20** |
| db/db, αCTGF (n = 14) | 177.4 ± 4.5* | 2.76 ± 0.31^Δ | 0.98 ± 0.09^□ |

Data are expressed as mean ± SEM.
**$P < 0.01$ vs. db/+ mice.
*$P < 0.01$ vs. db/+ mice and $P < 0.05$ cIgG-treated db/db mice.
^Δ$P < 0.01$ vs. cIgG-treated db/db mice.
^□$P < 0.01$ vs. db/+ mice and cIgG-treated db/db mice.

Figure 2:
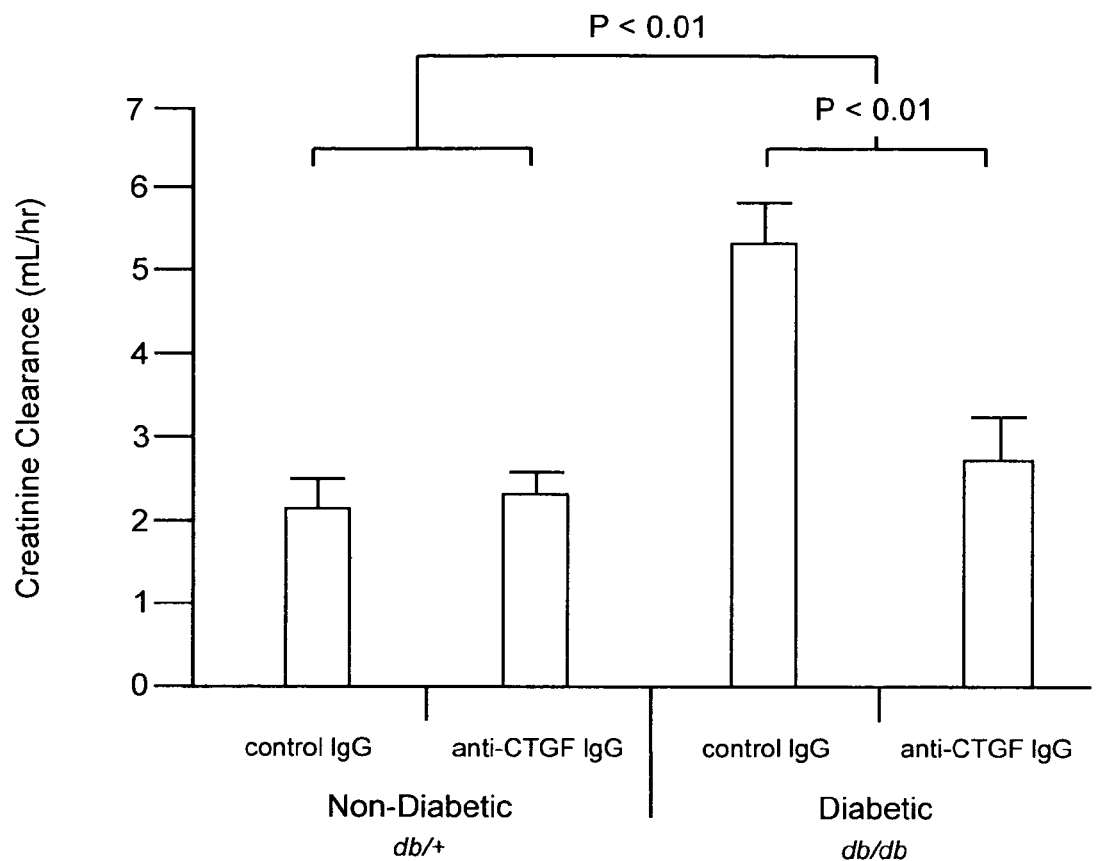
FIG. 2 shows anti-CTGF antibody administration reduced creatinine clearance in diabetic db/db mice.
Figure 3:
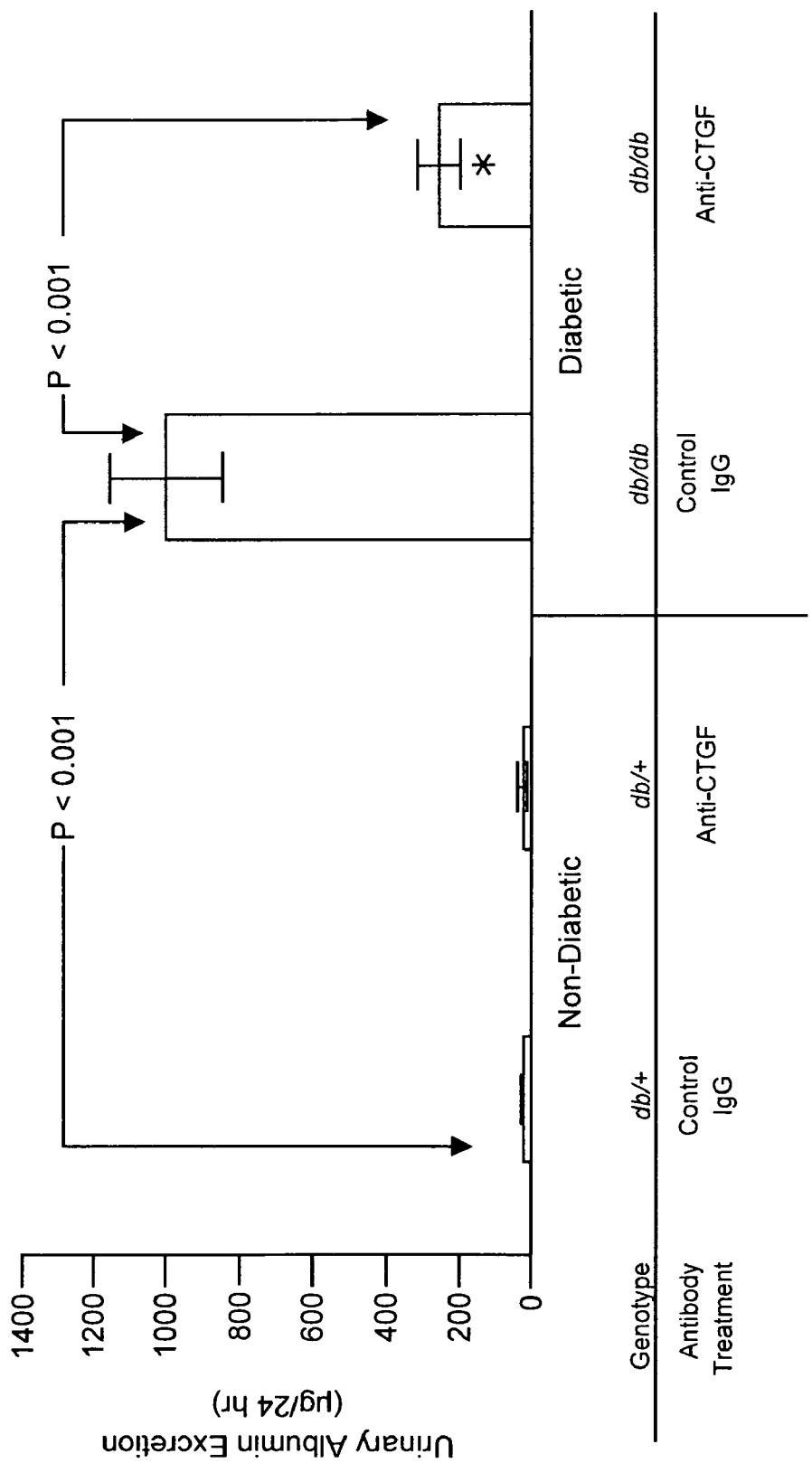
FIG. 3 shows anti-CTGF antibody administration reduced urinary albumin excretion in diabetic db/db mice.

As shown in Table 2, db/db mice exhibited hyperfunctioning kidneys as indicated by renal enlargement (i.e., increased kidney weight) (FIG. 1), increased creatinine clearance (FIG. 2), and increased urinary albumin excretion (FIG. 3,*P<0.01 vs. anti-CTGF-treated db/+). Diabetic animals treated with anti-CTGF antibody showed reduced kidney weight gain compared to diabetic animals treated with cIgG.

Creatinine clearance in cIgG-treated db/db animals was approximately twice the value observed in db/+animals, indicating impaired renal function, hypertrophy, and hyperfiltration in diabetic animals. The urinary albumin excretion was also increased in diabetic db/db animals compared to the urinary albumin excretion observed in non-diabetic db/+animals. The db/db animals treated with anti-CTGF antibody had creatinine clearance and urinary albumin excretion levels markedly lower than those observed in the cTgG-treated db/db animals. Specifically, the anti-CTGF treated diabetic mice had creatinine clearance levels 82% below that seen in the cIgG-treated diabetic mice. The anti-CTGF treated diabetic mice had urinary albumin excretion levels 69% below that seen in the cIgG-treated diabetic mice. These results provide evidence of a dramatic improvement in kidney function in the anti-CTGF antibody treated mice. Treatment of non-diabetic animals using methods of the invention showed no adverse effects on kidney weight or function. These data showed that administration of anti-CTGF antibody to diabetic animals resulted in reduced kidney weight gain, creatinine clearance, and urinary albumin excretion.

Figure 5:
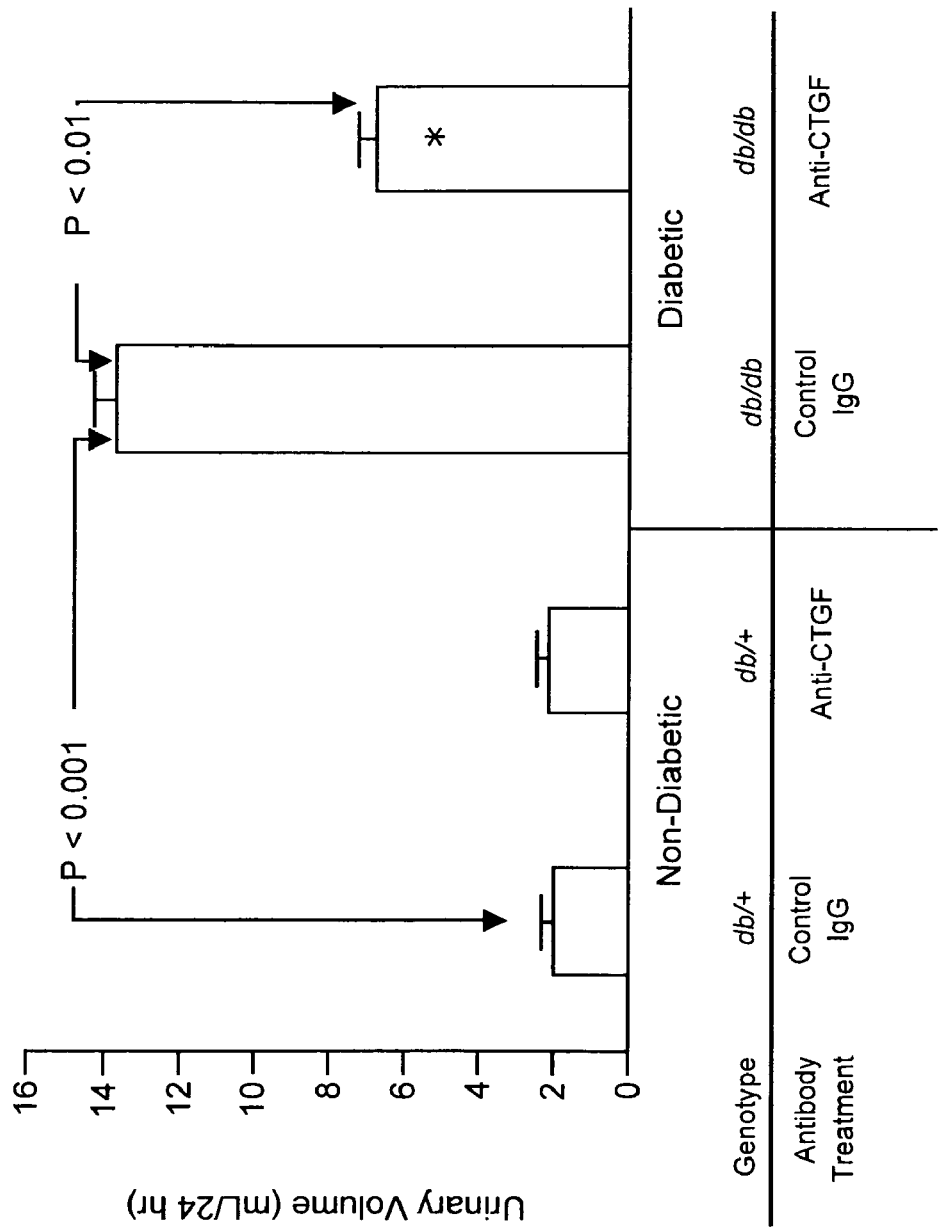
FIG. 5 shows anti-CTGF antibody administration reduced urine volume in diabetic db/db mice.

Further, diabetic (db/db) mice showed increased urine volume compared to non-diabetic (db/+) mice. Administration of anti-CTGF antibody as described above reduced urine volume in diabetic (db/db) mice. (See FIG. 5,*P<0.01 vs. anti-CTGF-treated db/+.) This data indicated that administration of anti-CTGF antibody to diabetic animals reduced urinary volume. These results also indicated that inhibition of CTGF provides a method for reducing increased urinary volume associated with diabetic nephropathy, and therefore provides a method for improving kidney function.

Figure 6:
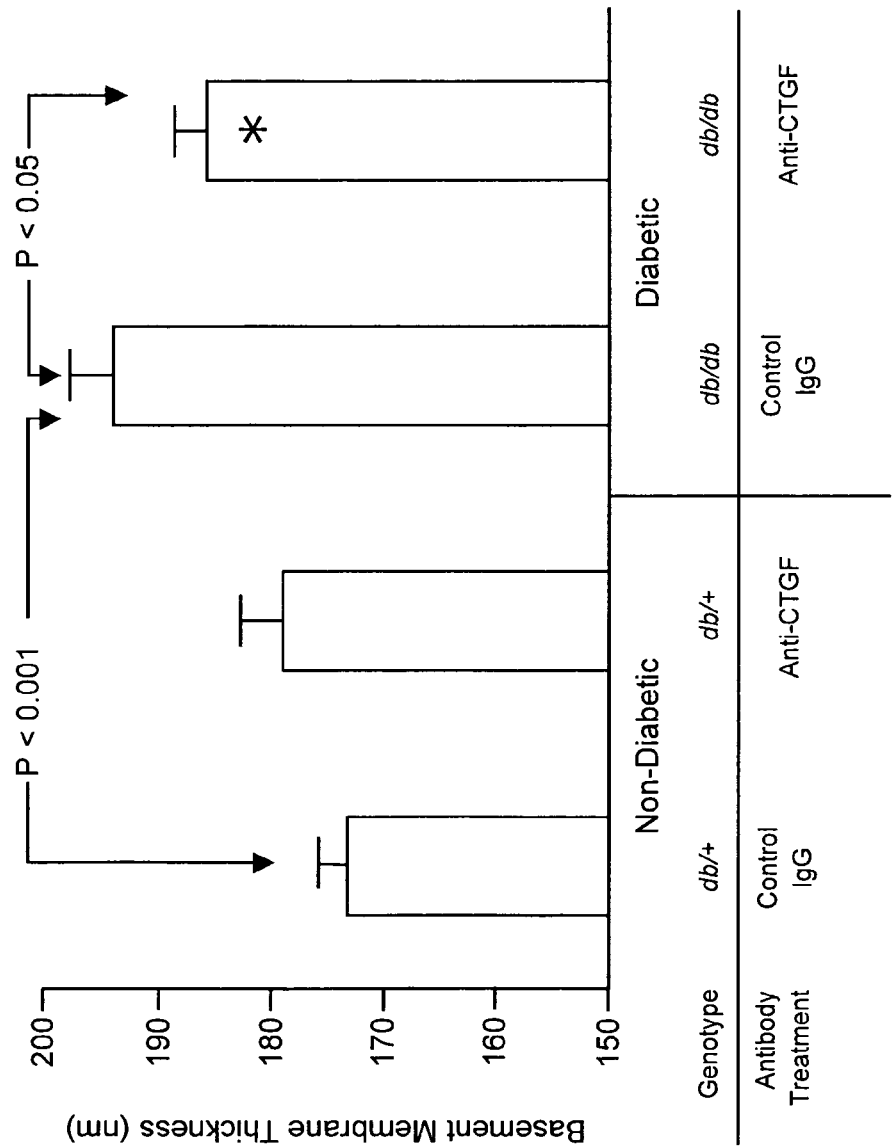
FIG. 6 shows anti-CTGF antibody administration reduced basement membrane thickening in kidneys of diabetic db/db mice.

Analysis of changes in glomerular volume (e.g., reduction in glomerular volume expansion) and basement membrane thickening further demonstrated the efficacy of inhibition of CTGF in treating and preventing the development and progression of diabetic nephropathy. As shown in FIG. 6 (*not different from anti-CTGF-treated db/+), treatment of diabetic (db/db) animals with anti-CTGF antibody reduced basement membrane thickening.

Taken together, these data showed that treatment of diabetic (db/db) animals with anti-CTGF antibody reduced kidney hypertrophy (as evidenced by lower kidney weight in anti-CTGF treated diabetic animals) and restored kidney function (as evidenced by a reduced increase in creatinine clearance and urinary excretion rate in anti-CTGF treated diabetic animals). These results also indicated that inhibition of CTGF provided a method for reducing glomerular permeability and hyperfiltration, as well as reducing mesangial expansion and basement membrane thickening. Therefore, inhibition of CTGF provides a therapeutic approach for treating early stage features of diabetic nephropathy.

Example 2

CTGF Implicated in Early Stage Features of Progressive Vitreoretinal Disorders

The association between CTGF and ocular disease, including retinal disorders, has been previously established. (See, e.g., International Publication No. WO 03/049773.) Here, the relationship between ocular concentrations of CTGF and VEGF and the degree of neovascularization and fibrosis were examined to determine the correlation, if any, between CTGF and VEGF expression in vitreous. A correlation would be suggestive of CTGF involvement in both early stage and late stage aspects of ocular disorders. Undiluted vitreous samples (0.5 to 1 ml) were obtained at the start of a pars plana vitrectomy in patients with proliferative vitreoretinopathy (PVR), proliferative diabetic retinopathy (PDR), macular pucker, or macular hole. Samples of vitreous fluids were collected in sterile tubes, immediately frozen in dry ice, and stored at −80° C. until assayed for CTGF and VEGF.

Neovascularization associated with all retinal disorders was graded as follows: grade 0, no neovascularization; grade 1, quiescent neovascularization, with only non-perfused, gliotic vessels present; and grade 2, active neovascularization, with perfused preretinal capillaries. (See Aiello et al. (1994) N Engl J Med 331:1480-1487.)

CTGF and VEGF levels in vitreous samples were measured by ELISA. Briefly, vitreous samples were centrifuged at 14,000 rpm for 15 minutes at 4° C. and the supernatant collected. CTGF levels were measured by sandwich ELISA using two monoclonal antibodies to human CTGF, each of which specifically recognizes a distinct region of the N-terminal portion of CTGF as follows. Microtiter plates were coated overnight at 4° C. with capture anti-CTGF monoclonal antibody (10 µg/ml) in coating buffer (50 mM sodium borate, pH 9.6). The plates were blocked with 100 µl 1% BSA in phosphate buffered saline for 2 hours at room temperature and then washed with wash buffer (phosphate buffered saline containing 0.05% Tween 20). Vitreous samples were diluted 5 times in assay buffer (50 mM TRIS, pH 7.7, 0.1% BSA, 4 mM $MgCl_2$, 400 mM $ZnCl_2$, 0.05% $NaN_3$, 50 mg/L sodium heparin, and 0.1% Triton X-100). To each well was added 50 µl of diluted vitreous sample together with 50 µl of biotinylated monoclonal anti-human CTGF detection antibody (diluted in assay buffer). The plates were incubated for 2 hours at 37° C., washed with wash buffer, and incubated with 100 µl/well streptavidin-conjugated alkaline phosphatase (1 µg/ml diluted in assay buffer) (Jackson Immunoresearch Laboratories) for 1 hour at room temperature. Following this incubation, the plates were washed with wash buffer and 100 µl of substrate solution (1 mg/ml, p-nitrophenyl phosphate, Sigma Chemical Co.) in diethanolamine buffer (1 M diethanolamine, 0.5 mM $MgCl_2$, 0.02% $NaN_3$, pH 9.8) was added to each well. Absorbance was read at 405 nm on a Bio-Rad microplate reader. Purified recombinant human CTGF was used as a standard. Vitreous levels of VEGF-165 were determined by a commercially available sandwich ELISA according to the manufacturer's instructions (R&D Systems).

Figure 4:
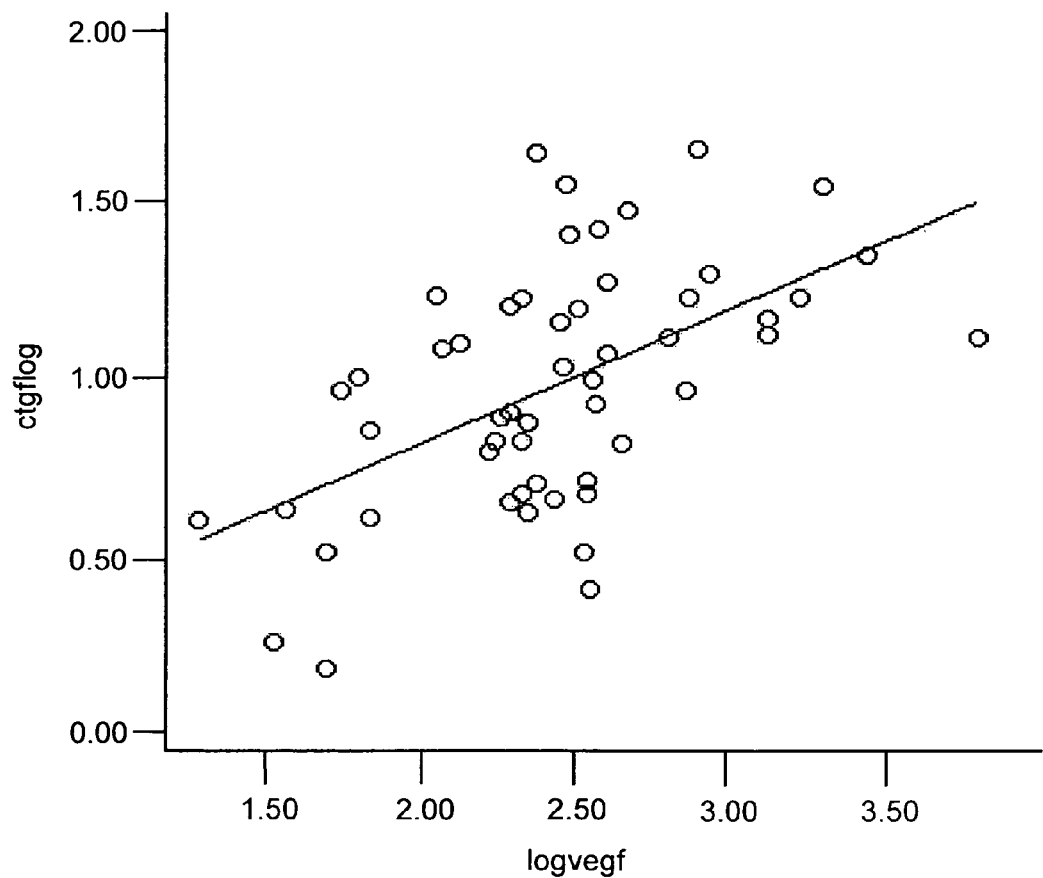
FIG. 4 shows the correlation between CTGF and VEGF levels in human vitreous.

A significant positive correlation between CTGF levels and the degree of neovascularization was observed (p=0.0153). As shown in Table 3 below, patients with the highest degree (grade 2) of neovascularization had significantly higher CTGF levels than patients with a lower degree (grade 0 or grade I) of neovascularization. FIG. 4 shows intravitreal CTGF and VEGF levels were positively correlated (r=0.544, p=0.001). Significantly, these results demonstrate for the first time a direct correlation between CTGF and VEGF levels measured from the same sample, at the same stage of disease.

TABLE 3

| Neovascularization Grade | CTGF Levels | 95% CI |
| --- | --- | --- |
| Grade 0 | 8.7 ng/ml | 6.9-11.0 |
| Grade 1 | 14.0 ng/ml | 11.2-17.5 |
| Grade 2 | 20.8 ng · ml | 16.2-26.9 |

Results from the experiments described above showed that CTGF is present in human vitreous and its concentration significantly and strongly correlated with the presence and degree of neovascularization and that vitreous levels of CTGF strongly correlated with vitreous levels of VEGF. While it has been established that CTGF is associated with the development and progression of ocular fibrosis and other late-stage aspects of retinal disease, the present results taken together with the results shown in Example 1 and Example 3 herein, implicate CTGF as well as VEGF as a critical factor in early stage development of progressive disease, including diabetic nephropathy and various vitreoretinal disorders. Therefore, the present invention provides methods for treating both early (e.g., neovascularization) and late (e.g., fibrosis) stages of retinopathies, such as, PVR, PDR, etc.

Example 3

Treatment of Late Stage Features of Diabetic Nephropathy

The effect of anti-CTGF therapy was examined in an animal model of late stage diabetic nephropathy. As has been previously described using this animal model, rats with diabetes mellitus exhibited high susceptibility to unilateral renal ischemia reperfusion, resulting in rapidly progressive nephropathy and end-stage renal failure, associated with development of fibrosis, atrophy of the kidney, and severely compromised glomerular filtration rate. (See, e.g., Melin et al. (1997) Kidney Int 52:985-991.) In this animal model of diabetes mellitus, ischemia severely impaired kidney function in diabetic rats. In this animal model, the renal effects on kidney function and pathology of hyperglycemia and ischemia are similar to those observed in human late stage diabetic nephropathy and end-stage renal disease (ESRD).

Diabetes mellitus was induced in male Sprague Dawley rats by a single i.v. dose of streptozotocin (STZ) (50 mg/kg). Unilateral renal ischemia reperfusion (IR) was achieved in one kidney by clamping the left renal artery for 30 minutes, thereby preventing blood flow to the left kidney. Treatment with anti-CTGF monoclonal antibody (i.p. 5 mg/kg) was initiated 1 day before renal ischemia reperfusion (i.e., 2 weeks after the development of diabetes) and continued 3 times per week for 10 weeks. Control animals not receiving anti-CTGF antibody were administered PBS (i.p. 5 ml/kg). Blood samples were obtained from the tail vein. Blood clinical chemistry, performed by Quality Clinical Labs, Inc. (Mountain View, Calif.), was analyzed at weeks 0, 4, 8, and 10. Total 24-hour urinary protein was determined at weeks 5 and 9. Individual rats were placed in metabolic cages and 24-hour urine specimens were collected. Urine volume was measured and urine protein was analyzed using a BCA Protein Assay Kit (Pierce Chemical Co.).

Glomerular filtration rate (GFR) is the most widely measurement of kidney function. Inulin clearance is a measurement of glomerular filtration rate. In these experiments, glomerular filtration rate (e.g., kidney function) was determined for individual kidneys by measurement of urine volume and inulin clearance. Urine was collected via a cannulated ureter and blood was collected from the femoral artery. Urine volume was estimated gravimetrically. Inulin concentration was determined using the Anthrone method. Inulin clearance, indicative of GFR, was determined using the formula: $(U_{conc} \times U_{vol})/S_{conc}$. At the end of the experiment, kidneys were removed for biochemical and histopathological evaluation.

Data are presented as mean +/− SEM. Data were compared within the experimental groups at each time point using one-way analysis of variance (ANOVA) and Student-Newman-Keuls method (SIGMASTAT). When only two groups were compared, a t-Test was used (Two-Sample Assuming Equal Variances analysis tool, Microsoft Excel). A value of P<0.05 was considered significant.

Animals administered a single dose of STZ became diabetic, as indicated by elevated blood glucose levels. Blood glucose levels increased from less than 200 mg/dL in control (non-STZ-treated) animals to levels greater than 600 mg/dL in STZ-treated animals, indicating that these animals were diabetic. Renal IR of non-diabetic (i.e., non-STZ-treated) animals did not increase blood glucose levels above that of control animals (data not shown). Blood glucose levels remained elevated in STZ-treated animals throughout the 10 weeks following unilateral renal IR. (Data not shown.)

Late Stage Proteinuria

Figure 7:
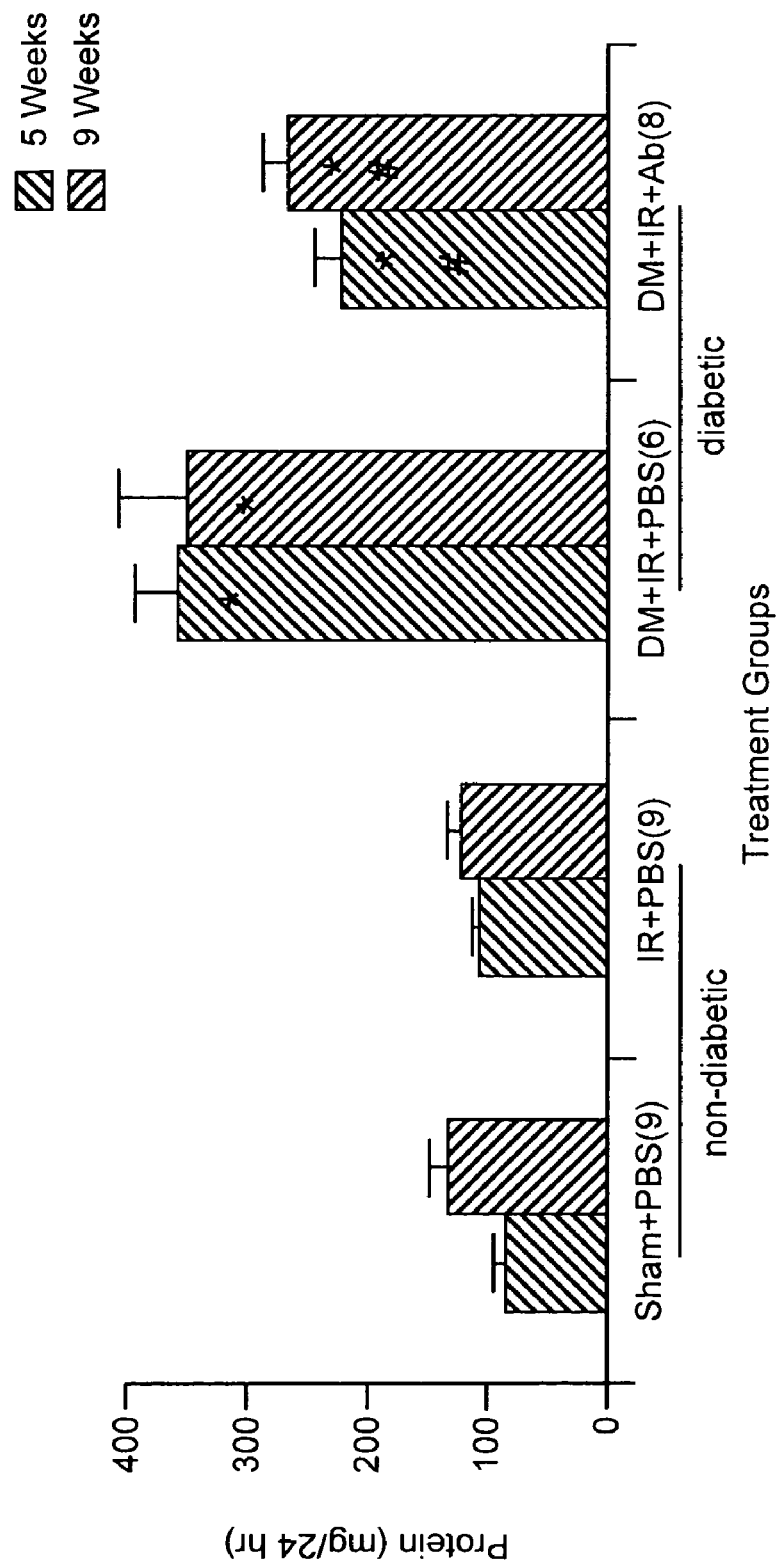
FIG. 7 shows anti-CTGF antibody administration reduced proteinuria in a rat model of diabetic nephropathy.

Microalbuminuria characteristic of early stage diabetic nephropathy progresses to macroalbuminuria and late stage proteinuria. In animals with diabetes mellitus, significant increases in 24-hour total urinary protein (i.e., late stage proteinuria) were observed, indicating increased glomerular hyperfiltration and development of renal failure. As shown in FIG. 7, total urine protein in non-diabetic animals (sham+PBS; IR+PBS) was approximately 100 mg/24-hours. (In FIG. 7, * higher than non-diabetic ($p<0.001$), # lower than DM+IR+PBS ($p<0.05$) at corresponding weeks.) Diabetic animals with renal IR, however, had total urine protein levels exceeding 350 mg/24-hours. Administration of anti-CTGF antibody to diabetic animals with renal IR resulted in a significant reduction in 24-hour total urine protein at weeks 5 and 9, to approximately 225 mg/24-hours and 250 mg/24-hours, respectively, compared to non-treated diabetic animals. (See FIG. 7.) This data showed that administration of an antibody to CTGF reduced proteinuria in diabetic animals. These results indicated that inhibition of CTGF provides a therapeutic means for decreasing kidney hyperfiltration. These results demonstrate for the first time that anti-CTGF therapy is useful for preventing the development and progression of late stage proteinuria.

Blood Urea-Nitrogen (BUN)

Figure 8:
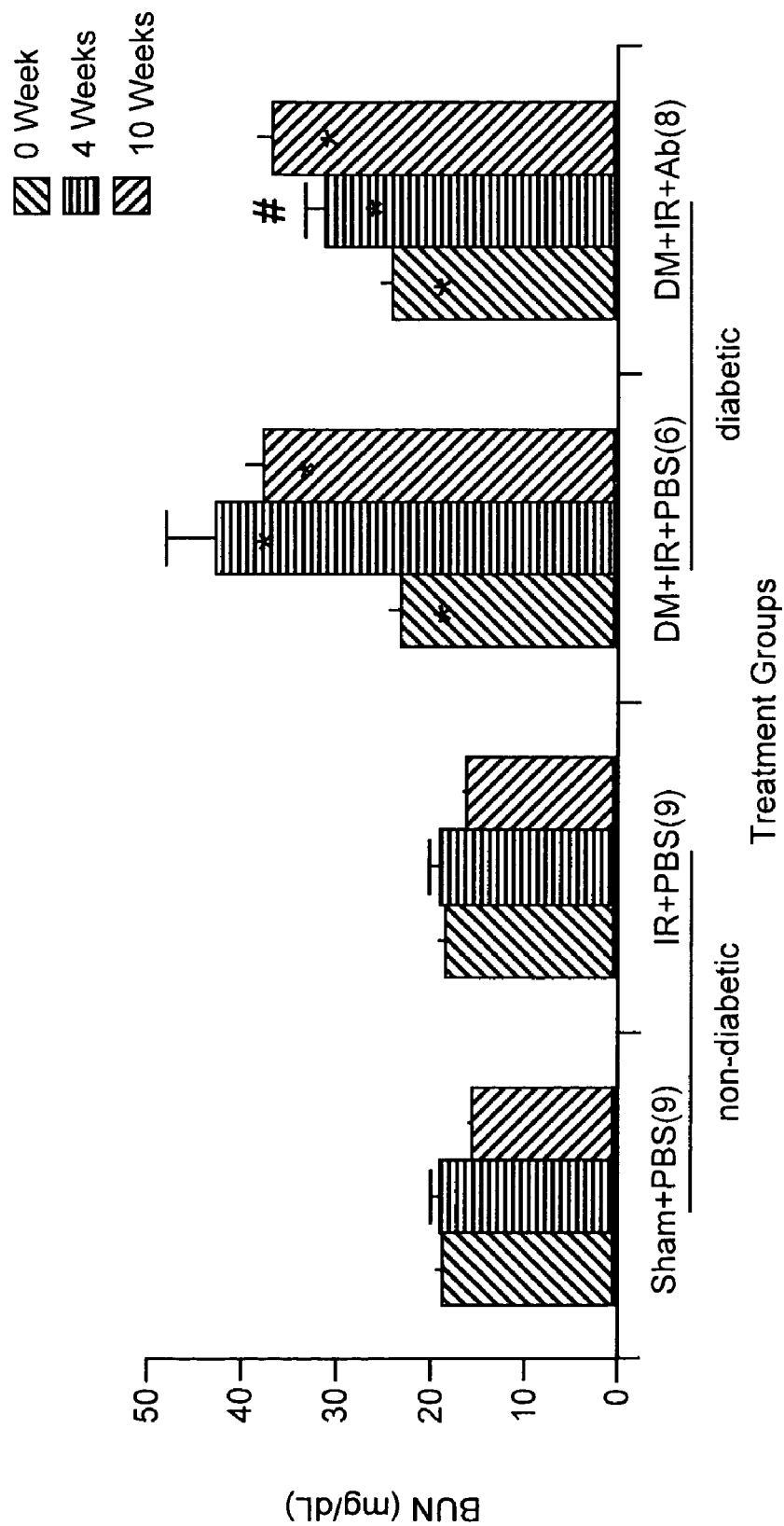
FIG. 8 shows anti-CTGF antibody administration reduced BUN levels in a rat model of diabetic nephropathy.

Increased BUN levels are indicative of impaired kidney function associated with late stage diabetic nephropathy. Significant increases in BUN levels were observed in these diabetic animals. BUN levels in control non-diabetic animals (sham+PBS; IR+PBS) were below 20 mg/dL at 0, 4, and 10 weeks of the study. In diabetic animals with renal IR, BUN levels increased from approximately 22 mg/dL at week zero, to greater than 40 mg/dL at 4 weeks. (See FIG. 8,* higher than sham+PBS and IR+PBS ($p<0.01$), # lower than DM+IR+PBS ($p<0.01$) at 4 weeks.) Administration of anti-CTGF monoclonal antibody to diabetic animals with renal IR resulted in a reduction of BUN levels at 4 weeks (to approximately 30 mg/dL) and at 10 weeks (to approximately 35 mg/dL), compared to that observed in diabetic animals without anti-CTGF antibody administration. (See FIG. 8.) These results showed for the first time that anti-CTGF therapy is useful for reducing BUN levels in diabetics, indicating that that inhibition of CTGF provides a therapeutic approach for improving kidney function.

Glomerular Filtration Rate

Glomerular filtration rate was determined for individual kidneys for each of the various experimental conditions described above. In control animals (i.e., non-diabetic, non-IR), GFR was greater than 0.3 mL/min/kidney/100 g. Non-diabetic animals with renal IR had a GFR of approximately 0.28 mL/min/kidney/100 g. Diabetic animals without renal IR had a GFR of approximately 0.17 mL/min/kidney/100 g. (Data not shown.)

Figure 9:
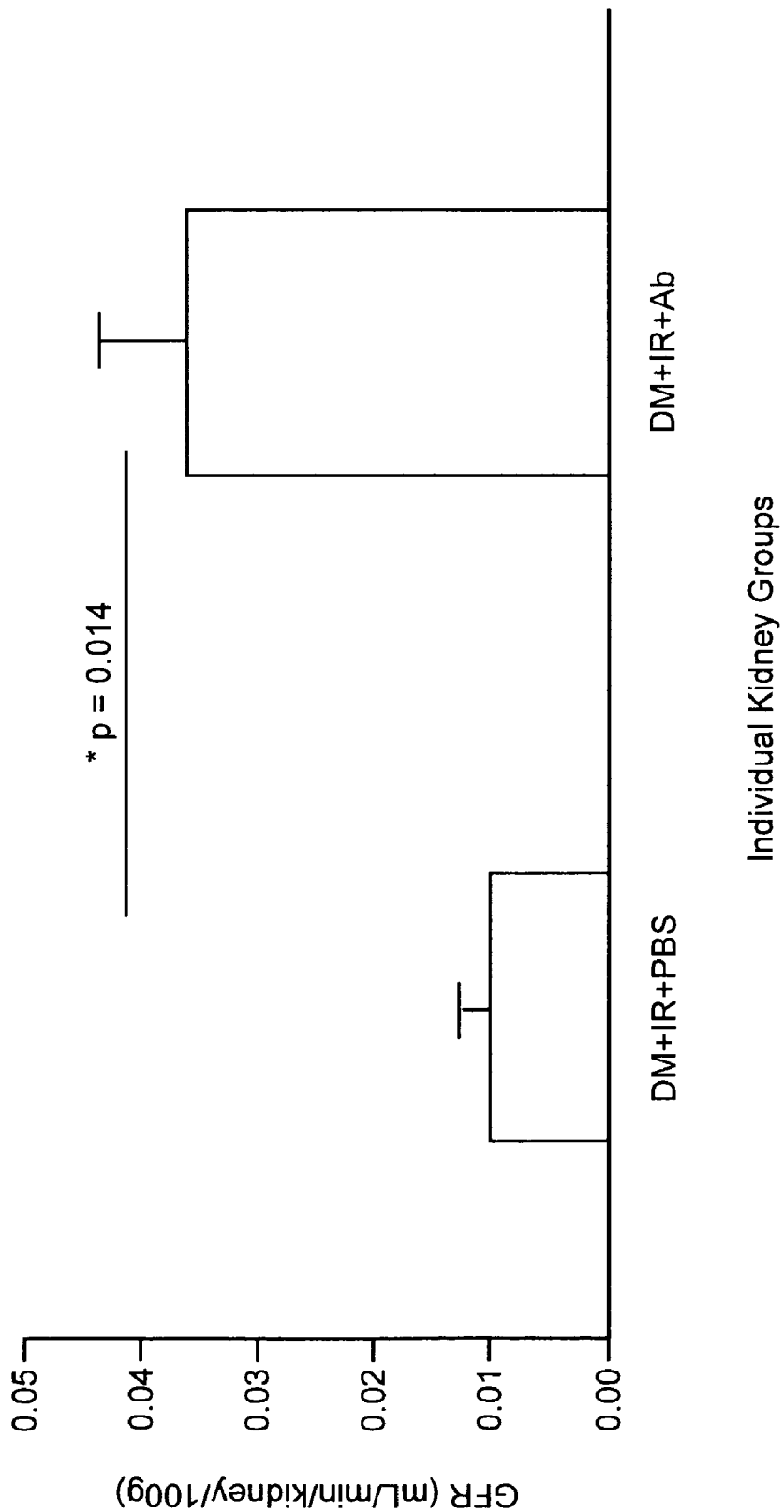
FIG. 9 shows anti-CTGF antibody administration improved glomerular filtration rate in a rat model of diabetic nephropathy.

Glomerular filtration rate was drastically reduced in the ischemic kidney of animals with diabetes mellitus at 10 weeks, to approximately 0.01 mL/min/kidney/100 g. (See FIG. 9.) Administration of anti-CTGF antibody significantly improved glomerular filtration rate in individual kidneys in diabetic animals affected by renal IR, to a level greater than 0.035 mL/min/kidney/100 g. This data showed that administration of an antibody to CTGF increased glomerular filtration rate in diabetic animals in late-stage renal disease. These results demonstrated for the first time that anti-CTGF therapy is effective at improving glomerular filtration rate in late stage diabetic nephropathy, and therefore, provides a therapeutic approach for improving kidney function in late-stage renal disease.

Various modifications of the invention, in addition to those shown and described herein, will become apparent to those skilled in the art from the foregoing description. Such modifications are intended to fall within the scope of the appended claims.

All references cited herein are hereby incorporated by reference herein in their entirety.

What is claimed is:

1. A method for reducing albuminuria in a subject having or at risk for having diabetes or diabetic nephropathy, the method comprising administering to the subject a therapeutically effective amount of an antibody that inhibits connective tissue growth factor, wherein the antibody is identical to the antibody produced by the cell line identified by ATCC Accession No. PTA-6006.

2. The method of claim 1, wherein the albuminuria is microalbuminuria.

3. The method of claim 1, wherein the albuminuria is macroalbuminuria.

4. A method for reducing urinary albumin excretion in a subject having or at risk for having diabetes or diabetic nephropathy, the method comprising administering to the subject a therapeutically effective amount of an antibody that inhibits connective tissue growth factor, wherein the antibody is identical to the antibody produced by the cell line identified by ATCC Accession No. PTA-6006.

* * * * *